(12) United States Patent
Say

(10) Patent No.: US 11,224,367 B2
(45) Date of Patent: Jan. 18, 2022

(54) SENSOR MODULE AND METHOD OF USING A SENSOR MODULE

(71) Applicant: PEPEX BIOMEDICAL, INC., St. Louis, MO (US)

(72) Inventor: James L. Say, Breckenridge, CO (US)

(73) Assignee: PEPEX BIOMEDICAL, INC., St. Louis, MO (US)

(*) Notice: Subject to any disclaimer, the term of this patent is extended or adjusted under 35 U.S.C. 154(b) by 626 days.

(21) Appl. No.: 14/649,132

(22) PCT Filed: Dec. 3, 2013

(86) PCT No.: PCT/US2013/072846
§ 371 (c)(1),
(2) Date: Jun. 2, 2015

(87) PCT Pub. No.: WO2014/089058
PCT Pub. Date: Jun. 12, 2014

(65) Prior Publication Data
US 2015/0313521 A1 Nov. 5, 2015

Related U.S. Application Data

(60) Provisional application No. 61/732,783, filed on Dec. 3, 2012.

(51) Int. Cl.
*A61B 5/15* (2006.01)
*A61B 5/157* (2006.01)
(Continued)

(52) U.S. Cl.
CPC .... *A61B 5/150396* (2013.01); *A61B 5/14532* (2013.01); *A61B 5/14865* (2013.01);
(Continued)

(58) Field of Classification Search
USPC .......................................................... 600/347
See application file for complete search history.

(56) References Cited

U.S. PATENT DOCUMENTS

| | | |
|---|---|---|
| 1,454,224 A | 5/1923 | Schmidt |
| 2,291,720 A | 8/1942 | Hukle |

(Continued)

FOREIGN PATENT DOCUMENTS

| | | |
|---|---|---|
| CA | 2050677 C | 3/1992 |
| DE | 4105222 A1 | 8/1992 |

(Continued)

OTHER PUBLICATIONS

European Search Report for 09826755.2 dated Oct. 5, 2012.
(Continued)

*Primary Examiner* — Christian Jang
*Assistant Examiner* — Mitchell E Alter
(74) *Attorney, Agent, or Firm* — Merchant & Gould P.C.

(57) ABSTRACT

A sensor module is disclosed herein. The sensor module includes a skin piercing member carried by the carrier. The skin piercing member has a skin piercing end positioned opposite from a base end. The skin piercing member defines a lumen that extends along the central longitudinal axis from the skin piercing end toward the base end and the lumen having a lumen axis. The sensor module also includes a blood sample analysis zone located entirely within the lumen of the skin piercing member and a capillary flow stop for stopping capillary flow at a predetermined location within the lumen of the skin piercing member. The sensor module includes an elongated working electrode positioned within the lumen. The working electrode has a length that extends along the lumen axis where at least a section of the working electrode is positioned within the analysis zone. The working electrode includes sensing chemistry.

31 Claims, 13 Drawing Sheets

(51) Int. Cl.
*A61B 5/145* (2006.01)
*A61B 5/151* (2006.01)
*A61B 5/00* (2006.01)
*A61B 5/1486* (2006.01)

(52) U.S. Cl.
CPC ........ *A61B 5/157* (2013.01); *A61B 5/150022* (2013.01); *A61B 5/15105* (2013.01); *A61B 5/15142* (2013.01); *A61B 5/150213* (2013.01); *A61B 5/150389* (2013.01); *A61B 5/6848* (2013.01); *A61B 5/150755* (2013.01); *A61B 2560/0468* (2013.01)

(56) References Cited

U.S. PATENT DOCUMENTS

| | | |
|---|---|---|
| 3,170,968 A | 2/1965 | Rokunohe et al. |
| 3,766,910 A | 10/1973 | Lake |
| 3,823,035 A | 7/1974 | Sanders |
| 4,008,717 A | 2/1977 | Kowarski |
| 4,073,974 A | 2/1978 | Albarino et al. |
| 4,224,125 A | 9/1980 | Nakamura et al. |
| 4,255,487 A | 3/1981 | Sanders |
| 4,321,057 A | 3/1982 | Buckles |
| 4,399,099 A | 8/1983 | Buckles |
| 4,439,303 A | 3/1984 | Cocchi |
| 4,545,283 A | 10/1985 | Sandberg et al. |
| 4,545,382 A | 10/1985 | Higgins et al. |
| 4,545,835 A | 10/1985 | Gusack et al. |
| 4,552,840 A | 11/1985 | Riffer |
| 4,573,968 A | 3/1986 | Parker |
| 4,640,821 A | 2/1987 | Mody et al. |
| 4,671,288 A | 6/1987 | Gough |
| 4,704,311 A | 11/1987 | Pickering et al. |
| 4,734,184 A | 3/1988 | Burleigh et al. |
| 4,762,603 A | 8/1988 | Morin |
| 4,805,624 A | 2/1989 | Yao et al. |
| 4,820,399 A | 4/1989 | Klainer et al. |
| 4,824,206 A | 5/1989 | Saxena |
| 4,833,083 A | 7/1989 | Klainer |
| 4,846,548 A | 7/1989 | Klainer |
| 4,880,752 A | 11/1989 | Keck et al. |
| 4,908,115 A | 3/1990 | Morita et al. |
| 4,919,649 A | 4/1990 | Timothy et al. |
| 4,927,516 A | 5/1990 | Yamaguchi et al. |
| 4,945,896 A | 8/1990 | Gade |
| 4,974,929 A | 12/1990 | Curry |
| 4,981,779 A | 1/1991 | Wagner |
| 5,001,054 A | 3/1991 | Wagner |
| 5,002,651 A | 3/1991 | Shaw et al. |
| 5,004,583 A | 4/1991 | Guruswamy et al. |
| RE33,677 E | 8/1991 | Vazirani |
| 5,047,044 A | 9/1991 | Smith et al. |
| 5,112,455 A | 5/1992 | Cozzette et al. |
| 5,131,138 A | 7/1992 | Crouse |
| 5,164,229 A | 11/1992 | Hay et al. |
| 5,165,406 A | 11/1992 | Wong |
| 5,165,407 A | 11/1992 | Wilson et al. |
| 5,171,689 A | 12/1992 | Kawaguri et al. |
| 5,186,808 A | 2/1993 | Yamaguchi et al. |
| 5,205,920 A | 4/1993 | Oyama et al. |
| 5,217,533 A | 6/1993 | Hay et al. |
| 5,220,920 A | 6/1993 | Gharib |
| 5,243,982 A | 9/1993 | Möstl et al. |
| 5,244,636 A | 9/1993 | Walt et al. |
| 5,250,264 A | 10/1993 | Walt et al. |
| 5,262,035 A | 11/1993 | Gregg et al. |
| 5,264,092 A | 11/1993 | Skotheim et al. |
| 5,264,103 A | 11/1993 | Yoshioka et al. |
| 5,264,104 A | 11/1993 | Gregg et al. |
| 5,264,105 A | 11/1993 | Gregg et al. |
| 5,269,891 A | 12/1993 | Colin |
| 5,271,815 A | 12/1993 | Wong |
| 5,271,820 A | 12/1993 | Kinlen et al. |
| 5,277,872 A | 1/1994 | Bankert et al. |
| 5,286,362 A | 2/1994 | Hoenes et al. |
| 5,298,144 A | 3/1994 | Spokane |
| 5,298,741 A | 3/1994 | Walt et al. |
| 5,320,725 A | 6/1994 | Gregg et al. |
| 5,320,814 A | 6/1994 | Walt et al. |
| 5,330,634 A | 7/1994 | Wong et al. |
| 5,356,786 A | 10/1994 | Heller et al. |
| 5,366,527 A | 11/1994 | Amos et al. |
| 5,372,133 A | 12/1994 | Hogen esch |
| D354,347 S | 1/1995 | Knute et al. |
| D354,559 S | 1/1995 | Knute et al. |
| 5,384,028 A | 1/1995 | Ito |
| 5,386,828 A | 2/1995 | Owens et al. |
| 5,395,504 A | 3/1995 | Saurer et al. |
| 5,422,246 A | 6/1995 | Koopal et al. |
| 5,431,174 A | 7/1995 | Knute |
| 5,437,973 A | 8/1995 | Vadgama et al. |
| 5,503,728 A | 4/1996 | Kaneko et al. |
| 5,505,828 A | 4/1996 | Wong et al. |
| 5,512,159 A | 4/1996 | Yoshioka et al. |
| 5,515,848 A | 5/1996 | Corbett et al. |
| 5,543,012 A | 8/1996 | Watson et al. |
| 5,575,403 A | 11/1996 | Charlton et al. |
| 5,591,139 A | 1/1997 | Lin et al. |
| 5,593,852 A | 1/1997 | Heller et al. |
| 5,605,152 A | 2/1997 | Slate et al. |
| 5,609,749 A | 3/1997 | Yamauchi et al. |
| 5,645,710 A | 7/1997 | Shieh |
| 5,656,241 A | 8/1997 | Seifert et al. |
| 5,704,354 A | 1/1998 | Preidel et al. |
| 5,720,924 A | 2/1998 | Eikmeier et al. |
| 5,777,060 A | 7/1998 | Van Antwerp |
| 5,800,350 A | 9/1998 | Coppleson et al. |
| 5,810,199 A | 9/1998 | Charlton et al. |
| 5,814,601 A | 9/1998 | Winslow et al. |
| 5,849,415 A | 12/1998 | Shalaby et al. |
| 5,863,800 A | 1/1999 | Eikmeier et al. |
| 5,900,215 A | 5/1999 | Seifert et al. |
| 5,951,764 A | 9/1999 | Hay et al. |
| 5,971,941 A | 10/1999 | Simons et al. |
| 5,972,199 A | 10/1999 | Heller et al. |
| 5,982,959 A | 11/1999 | Hopenfeld |
| 5,997,501 A | 12/1999 | Gross et al. |
| 6,004,818 A | 12/1999 | Freilich et al. |
| 6,036,924 A | 3/2000 | Simons et al. |
| 6,044,665 A | 4/2000 | Lysson et al. |
| 6,048,352 A | 4/2000 | Douglas et al. |
| D424,696 S | 5/2000 | Ray et al. |
| D426,638 S | 6/2000 | Ray et al. |
| 6,071,294 A | 6/2000 | Simons et al. |
| 6,071,391 A | 6/2000 | Gotoh et al. |
| 6,083,710 A | 7/2000 | Heller et al. |
| 6,099,484 A | 8/2000 | Douglas et al. |
| 6,103,033 A | 8/2000 | Say et al. |
| 6,103,199 A | 8/2000 | Bjornson et al. |
| 6,104,940 A | 8/2000 | Watanabe et al. |
| 6,107,083 A | 8/2000 | Collins et al. |
| 6,120,676 A | 9/2000 | Heller et al. |
| 6,143,164 A | 11/2000 | Heller et al. |
| 6,241,863 B1 | 6/2001 | Montbouquette |
| 6,299,757 B1 | 10/2001 | Feldman et al. |
| 6,329,161 B1 | 12/2001 | Heller et al. |
| 6,338,790 B1 | 1/2002 | Feldman et al. |
| 6,349,229 B1 | 2/2002 | Watanabe et al. |
| 6,375,627 B1 | 4/2002 | Mauze et al. |
| 6,379,317 B1 | 4/2002 | Kintzig et al. |
| 6,461,496 B1 | 10/2002 | Feldman et al. |
| 6,464,849 B1 | 10/2002 | Say et al. |
| 6,484,045 B1 | 11/2002 | Holker et al. |
| 6,500,144 B1 | 12/2002 | Russell et al. |
| 6,503,381 B1 | 1/2003 | Gotoh et al. |
| 6,560,471 B1 | 5/2003 | Heller et al. |
| 6,561,989 B2 | 5/2003 | Whitson |
| 6,576,101 B1 | 6/2003 | Heller et al. |
| 6,576,102 B1 | 6/2003 | Rappin et al. |
| 6,591,125 B1 | 7/2003 | Buse et al. |
| 6,592,745 B1 | 7/2003 | Feldman et al. |
| 6,607,658 B1 | 8/2003 | Heller et al. |
| 6,610,978 B2 | 8/2003 | Yin et al. |

(56) References Cited

U.S. PATENT DOCUMENTS

| | | |
|---|---|---|
| 6,616,819 B1 | 9/2003 | Liamos et al. |
| 6,618,934 B1 | 9/2003 | Feldman et al. |
| 6,620,112 B2 | 9/2003 | Klitmose |
| 6,676,816 B2 | 1/2004 | Mao et al. |
| 6,706,159 B2 | 3/2004 | Moerman et al. |
| 6,707,554 B1 | 3/2004 | Miltner et al. |
| 6,740,214 B1 | 5/2004 | Dobson et al. |
| 6,749,740 B2 | 6/2004 | Liamos et al. |
| 6,783,502 B2 | 8/2004 | Orloff et al. |
| 6,840,912 B2 | 1/2005 | Kloepfer et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,965,791 B1 | 11/2005 | Hitchcock et al. |
| 7,008,799 B1 | 3/2006 | Zimmer et al. |
| 7,058,437 B2 | 6/2006 | Buse et al. |
| 7,211,437 B2 | 5/2007 | Schabbach et al. |
| 7,264,139 B2 | 9/2007 | Brickwood et al. |
| 7,282,705 B2 | 10/2007 | Brennen |
| 7,299,081 B2 | 11/2007 | Mace et al. |
| 7,322,942 B2 | 1/2008 | Roe |
| 7,335,294 B2 | 2/2008 | Heller et al. |
| 7,344,499 B1 | 3/2008 | Prausnitz et al. |
| 7,378,007 B2 | 5/2008 | Moerman et al. |
| 7,396,334 B2 | 7/2008 | Kuhr et al. |
| 7,585,278 B2 | 9/2009 | Aceti et al. |
| 7,723,099 B2 | 5/2010 | Miller et al. |
| 7,740,581 B2 | 6/2010 | Buse et al. |
| 7,828,749 B2 | 11/2010 | Douglas et al. |
| 7,829,023 B2 | 11/2010 | Burke et al. |
| 7,860,544 B2 | 12/2010 | Say et al. |
| 8,702,932 B2 | 4/2014 | Say |
| 8,828,200 B2 | 9/2014 | Marquant et al. |
| 9,044,178 B2 | 6/2015 | Say |
| 9,459,228 B2 | 10/2016 | Say |
| 9,746,440 B2 | 8/2017 | Say |
| 2002/0040208 A1 | 4/2002 | Flaherty et al. |
| 2002/0061589 A1* | 5/2002 | King .................. A61N 1/325 |
| | | 435/446 |
| 2002/0098124 A1 | 7/2002 | Bentsen et al. |
| 2003/0083686 A1 | 5/2003 | Freeman et al. |
| 2003/0211619 A1 | 11/2003 | Olson et al. |
| 2004/0087033 A1 | 5/2004 | Schembri |
| 2004/0102717 A1 | 5/2004 | Qi |
| 2004/0236251 A1 | 11/2004 | Roe et al. |
| 2005/0004438 A1 | 1/2005 | Ward et al. |
| 2005/0023137 A1 | 2/2005 | Bhullar et al. |
| 2005/0067737 A1 | 3/2005 | Rappin et al. |
| 2005/0089944 A1 | 4/2005 | Shieh et al. |
| 2005/0143635 A1 | 6/2005 | Kamath et al. |
| 2005/0196747 A1 | 9/2005 | Stiene |
| 2005/0197548 A1 | 9/2005 | Dietiker |
| 2005/0238537 A1 | 10/2005 | Say et al. |
| 2006/0241517 A1 | 10/2006 | Fowler et al. |
| 2007/0027384 A1 | 2/2007 | Brister et al. |
| 2007/0027385 A1 | 2/2007 | Brister et al. |
| 2007/0032717 A1* | 2/2007 | Brister .............. A61B 5/14865 |
| | | 600/347 |
| 2007/0093704 A1 | 4/2007 | Brister et al. |
| 2007/0123803 A1 | 5/2007 | Fujiwara et al. |
| 2007/0149897 A1 | 6/2007 | Ghesquiere et al. |
| 2007/0197889 A1 | 8/2007 | Brister et al. |
| 2007/0199818 A1 | 8/2007 | Petyt et al. |
| 2007/0218281 A1 | 9/2007 | Demir et al. |
| 2007/0261958 A1 | 11/2007 | Jiang et al. |
| 2008/0017645 A1 | 1/2008 | Garagiola |
| 2008/0097546 A1 | 4/2008 | Powers et al. |
| 2008/0167578 A1 | 7/2008 | Bryer et al. |
| 2008/0275318 A1* | 11/2008 | Lastovich .......... A61B 5/14532 |
| | | 600/316 |
| 2008/0319314 A1 | 12/2008 | Hill et al. |
| 2009/0021901 A1 | 1/2009 | Stothers |
| 2009/0032760 A1 | 2/2009 | Muscatell |
| 2009/0062767 A1 | 3/2009 | Van Antwerp et al. |
| 2009/0069654 A1 | 3/2009 | Yasuzawa et al. |
| 2009/0178923 A1* | 7/2009 | Marquant .......... A61B 5/14532 |
| | | 204/403.01 |
| 2009/0257917 A1 | 10/2009 | Nakamura et al. |
| 2010/0018869 A1 | 1/2010 | Feldman et al. |
| 2010/0018871 A1 | 1/2010 | Feldman et al. |
| 2010/0051479 A1 | 3/2010 | Heller et al. |
| 2010/0059372 A1 | 3/2010 | Heller et al. |
| 2010/0059373 A1 | 3/2010 | Heller et al. |
| 2010/0072063 A1 | 3/2010 | Heller et al. |
| 2010/0072064 A1 | 3/2010 | Heller et al. |
| 2010/0326842 A1 | 12/2010 | Mazza et al. |
| 2011/0028815 A1 | 2/2011 | Simpson et al. |
| 2011/0086373 A1 | 4/2011 | Wallace-Davis et al. |
| 2011/0172559 A1 | 7/2011 | Fei et al. |
| 2011/0180405 A1* | 7/2011 | Chinnayelka ........ A61B 5/1411 |
| | | 204/403.15 |
| 2011/0189762 A1* | 8/2011 | Say .................... G01N 27/3275 |
| | | 435/287.1 |
| 2011/0203941 A1 | 8/2011 | Say |
| 2011/0265944 A1 | 11/2011 | Say |
| 2011/0266149 A1 | 11/2011 | Say |
| 2011/0270061 A1 | 11/2011 | Say |
| 2012/0046533 A1 | 2/2012 | Voskanyan et al. |
| 2012/0291254 A1 | 11/2012 | Say |
| 2013/0225957 A1* | 8/2013 | Kawamoto .......... A61B 5/1411 |
| | | 600/347 |
| 2014/0318988 A1 | 10/2014 | Say |
| 2015/0251174 A1* | 9/2015 | Ma ..................... B01L 3/021 |
| | | 422/520 |
| 2017/0067845 A1 | 3/2017 | Say et al. |
| 2018/0106750 A1 | 4/2018 | Say et al. |

FOREIGN PATENT DOCUMENTS

| | | | |
|---|---|---|---|
| DE | 20009392 U1 | 11/2000 | |
| DE | 10112384 A1 | 9/2002 | |
| DE | 102004060742 A1 | 7/2006 | |
| EP | 0 256 415 A2 | 2/1988 | |
| EP | 0 327 658 A1 | 8/1989 | |
| EP | 0 409 033 A2 | 1/1991 | |
| EP | 0 420 296 A1 | 4/1991 | |
| EP | 0 567 725 A1 | 11/1993 | |
| EP | 0 592 805 A2 | 4/1994 | |
| EP | 0 710 835 A2 | 5/1996 | |
| EP | 0 792 620 A2 | 9/1997 | |
| EP | 0 965 301 A1 | 12/1999 | |
| EP | 1 462 775 B1 | 12/2007 | |
| JP | 64-3552 | 1/1989 | |
| JP | 1-153952 | 6/1989 | |
| JP | 1-263537 | 10/1989 | |
| JP | 4-279854 | 10/1992 | |
| JP | 6-174946 | 6/1994 | |
| JP | 8-107890 | 4/1996 | |
| JP | 2007-202632 | 8/2007 | |
| JP | WO 2012043051 A1 * | 4/2012 | ........... A61B 5/1411 |
| WO | WO 89/07139 | 8/1989 | |
| WO | WO 90/10861 A1 | 9/1990 | |
| WO | WO 91/15993 | 10/1991 | |
| WO | WO 94/10553 | 5/1994 | |
| WO | WO 96/06947 | 3/1996 | |
| WO | WO 96/22730 | 8/1996 | |
| WO | WO 96/39616 | 12/1996 | |
| WO | WO 97/15827 | 5/1997 | |
| WO | WO 00/35340 | 6/2000 | |
| WO | WO 2005/051183 A1 | 6/2005 | |
| WO | 2007/037970 A1 | 4/2007 | |
| WO | WO 2007/091633 A1 | 8/2007 | |
| WO | WO 2008/017645 A1 | 2/2008 | |
| WO | WO 2008/118919 A1 | 10/2008 | |
| WO | WO 2009/032760 A2 | 3/2009 | |
| WO | WO 2009/051901 A2 | 4/2009 | |
| WO | WO 2010/056869 A2 | 5/2010 | |
| WO | WO 2010/056876 A2 | 5/2010 | |
| WO | WO 2010/056878 A2 | 5/2010 | |
| WO | 2011/003039 A2 | 1/2011 | |
| WO | 2012/043051 A1 | 4/2012 | |

(56) References Cited

FOREIGN PATENT DOCUMENTS

| WO | WO 2012/106060 A2 | 8/2012 |
|----|-------------------|--------|
| WO | 2014/025430 A2 | 2/2014 |

OTHER PUBLICATIONS

Gough et al., "Short-term In Vivo operation of a glucose sensor," *A.S.A.I.O. Transactions* (1986) 32 (1): 148-150. XP000009622.
International Search Report and Written Opinion for PCT/US2008/074649 dated Apr. 20, 2009.
International Search Report and Written Opinion for PCT/US2008/074644 dated May 14, 2009.
International Search Report and Written Opinion for PCT/US2009/064216 dated May 3, 2010.
International Search Report and Written Opinion for PCT/US2009/064225 dated May 4, 2010.
International Search Report and Written Opinion for PCT/US2009/064228 dated Jul. 1, 2010.
Jaraba et al., "NADH amperometric sensor based on poly(3-methylthiophene)-coated cylindrical carbon fiber microelectrodes: application to the enzymatic determination of L-lactate," *Electrochimica Acta.* (1998) 43 (23): 3555-3565.
Netchiporouk et al., "Properties of carbon fibre microelectrodes as a basis for enzyme biosensors," *Analytica Chimica Acta* (1995) 303: 275-283.
Sakslund et al, "Analysis of the factors determining the sensitivity of a miniaturized glucose biosensor made by codeposition of palladium and glucose oxidase onto an 8 μm carbon filter," *Journal of Electroanalytical Chemistry* (1996) 402: 149-160.
Sakslund et al., "Development and evaluation of glucose microsensors based on electrochemical codeposition of ruthenium and glucose oxidase onto carbon fiber microelectrodes," *Journal of Electroanalytical Chemistry* (1995) 397: 149-155.
International Search Report and Written Opinion for PCT/US2013/072846 dated Mar. 26, 2014.
Chinese Office Action and English translation thereof, Application No. 201380069383.1, dated Aug. 15, 2017, 18 pages.
European Search Report for corresponding European Patent Application No. 13860026.7, dated Dec. 23, 2016.
Extended European Search Report for Application No. 15802478.6, dated Feb. 22, 2018.
Hoey et al., "A Review on Aerosol-Based Direct-Write and Its Applications for Microelectronics," Journal of Nanotechnology, vol. 2012, Article ID 324380, 22 pages (2012).
Marinov et al., "Direct-Write Vapor Sensors on FR4 Plastic Substrates," IEEE Sensors Journal, vol. 7, No. 6, pp. 937-944 (Jun. 2007).
Young et al., "Future Opportunities for Advancing Glucose Test Device Electronics," Journal of Diabetes Science and Technology, vol. 5, Issue 5, pp. 1077-1086 (Sep. 2011).
Zhang, "Printed Electronics: Manufacturing Technologies and Applications Presentation Outline Introduction to Georgia Tech Manufacturing Institute Overview of printed electronics technology and applications Aerosol Jet Printing (AJP) process Application case studies," 54 pages (May 12, 2014).
Communication pursuant to Article 94(3) EPC, issued in European Patent Applicatio No. 13860026.7 (dated Aug. 5, 2021).

\* cited by examiner

SENSOR MODULE AND METHOD OF USING A SENSOR MODULE

This application is a National Stage Application of International Patent Application No. PCT/US2013/072846, filed Dec. 3, 2013, which claims benefit of U.S. Provisional Application No. 61/732,783, filed Dec. 3, 2012, which applications are incorporated herein by reference. To the extent appropriate, a claim of priority is made to each of the above disclosed applications.

TECHNICAL FIELD

The present disclosure relates generally to sensors. More particularly, the present disclosure relates to sensors for measuring bio-analyte concentrations in blood samples.

BACKGROUND

Electrochemical bio-sensors have been developed for sensing (e.g., detecting or measuring) bio-analyte concentrations in fluid samples. For example, U.S. Pat. Nos. 5,264,105; 5,356,786; 5,262,035; 5,320,725; and 6,464,849, which are hereby incorporated by reference in their entireties, disclose wired enzyme sensors for sensing analytes, such as lactate or glucose. Wired enzyme sensors have been widely used in blood glucose monitoring systems adapted for home use by diabetics to allow blood glucose levels to be closely monitored. Other example types of blood glucose monitoring systems are disclosed by U.S. Pat. Nos. 5,575,403; 6,379,317; and 6,893,545.

SUMMARY

In general terms, this disclosure is directed to a sensor and a method of using the same.

One aspect of the present disclosure relates to a sensor module that includes a carrier and a skin piecing member carried by the carrier. The skin piercing member has a skin piecing end positioned opposite from a base end. The skin piecing member defines a lumen that extends along the central longitudinal axis from the skin piercing end toward the base end where the lumen has a lumen axis. The sensor module includes a blood sample analysis zone located entirely within the lumen of the skin piercing member and a capillary flow stop for stopping capillary flow at a predetermined location within the lumen of the skin piercing member. The sensor module further includes an elongated working electrode positioned within the lumen. The working electrode has a length that extends along the lumen axis where at least a section of the working electrode is positioned within the analysis zone and the working electrode includes sensing chemistry.

Another aspect of the present disclosure relates to a sensor module including a carrier and a skin piercing member carried by the carrier. The skin piercing member has a skin piecing end positioned opposite from a base end. The skin piecing member defines a lumen that extends along the central longitudinal axis from the skin piercing end toward the base end and the lumen defines a lumen axis. The sensor module includes a blood sample analysis zone located within the lumen of the skin piercing member and an elongated working electrode positioned within the lumen. The working electrode having a length that extends along the lumen axis, at least a section of the working electrode is positioned within the analysis zone and the working electrode includes sensing chemistry. The working electrode has an end within 0.5 millimeters of a tip of the skin piercing member.

A further aspect of the present disclosure relates to a sensor module including a carrier movable relative to a base between a first position and second position and a skin piecing member carried by the carrier. The skin piercing member has a skin piecing end positioned opposite from a base end and the skin piercing member defines a lumen that extends along the central longitudinal axis from the skin piercing end toward the base end. The lumen defines a lumen axis. The sensor module includes a blood sample analysis zone located entirely within the lumen of the skin piercing member and an elongated working electrode positioned within the lumen. The working electrode has a length that extends along the lumen axis where at least a section of the working electrode is positioned within the analysis zone and the working electrode has sensing chemistry.

A further aspect of the present disclosure relates to a sensor module that includes a carrier and a skin piercing member carried by the carrier. The skin piercing member has a skin piercing end positioned opposite from a base end and the skin piercing member defines a lumen that extends along the central longitudinal axis from the skin piercing end toward the base end. The lumen defines a lumen axis. The sensor module includes a blood sample analysis zone located within the lumen of the skin piercing member and an elongated working electrode positioned within the lumen. The working electrode has a length that extends along the lumen axis where at least a section of the working electrode is positioned within the analysis zone. The working electrode includes sensing chemistry and is formed by a single fiber or wire.

A further aspect of the present disclosure relates to a method for taking a blood analyte reading that includes puncturing skin with a skin piercing member having a lumen and positioning a tip of the skin piercing member in a capillary blood field less than 3 millimeters beneath the skin. The method includes initiating blood flow into the lumen by a combination of vascular blood pressure and capillary action to passively bring a blood sample to an analysis zone entirely within the lumen and sensing the blood analyte in the analysis zone.

Still another aspect of the present disclosure relates to a device for sensing an analyte in a blood sample. The device includes an elongated working electrode having a first portion that is subcutaneous during testing and a second portion that extends outside the body during testing. The device is configured for a one time use in which one analyte reading is taken.

Another aspect of the present disclosure relates to a device for sensing an analyte in a blood sample. The device includes a working electrode formed by a single conductive fiber or wire having a first portion that is subcutaneous during testing and a second portion that extends outside the body during testing. The working electrode includes a layer of sensing chemistry on the first and second portions of the conductive fiber or wire.

A further aspect of the present disclosure relates to a device for sensing an analyte in a blood sample. The device includes a working electrode formed by a conductive fiber or wire having a first portion that is subcutaneous during testing and a second portion that extends outside the body during testing. The working electrode includes a layer of sensing chemistry on the first and second portions of the conductive fiber or wire. The device further includes a skin piercing member having a lumen in which the working electrode is positioned. The conductive fiber or wire has an outer diameter that is at least 10 percent as large as an outer diameter of the skin piercing member.

A further aspect of the present disclosure relates to a device for sensing an analyte in a blood sample. The device includes a working electrode formed by a conductive fiber or wire having a first portion that is subcutaneous during testing and a second portion that extends outside the body during testing. The working electrode includes a layer of sensing chemistry on the first and second portions of the conductive fiber or wire. The device includes a skin piercing member having a lumen in which the working electrode is positioned. The conductive fiber or wire has an outer diameter that is greater than 0.001 inches.

Another aspect of the present disclosure relates to a device for sensing an analyte in a blood sample. The device includes an elongated working electrode including a conductive fiber or wire having a first portion that is subcutaneous during testing and a second portion that extends outside the body during testing. The conductive fiber or wire has a cross-dimension greater than 0.001 inches.

Still another aspect of the present disclosure relates to a device for sensing an analyte in a blood sample. The device includes a working electrode formed by a conductive fiber or wire having a first portion that is subcutaneous during testing and a second portion that extends outside the body during testing. The working electrode includes a layer of sensing chemistry on the first and second portions of the conductive fiber or wire. The device further includes a skin piercing member having a lumen in which the working electrode is positioned. The device is configured such that a blood analysis zone of the device fills passively.

A variety of additional aspects will be set forth within the description that follows. The aspects can relate to individual features and to combinations of features. It is to be understood that both the foregoing general description and the following detailed description are exemplary and explanatory only and are not restrictive of the broad concepts upon which the embodiments disclosed herein are based.

DETAILED DESCRIPTION

Figure 1:
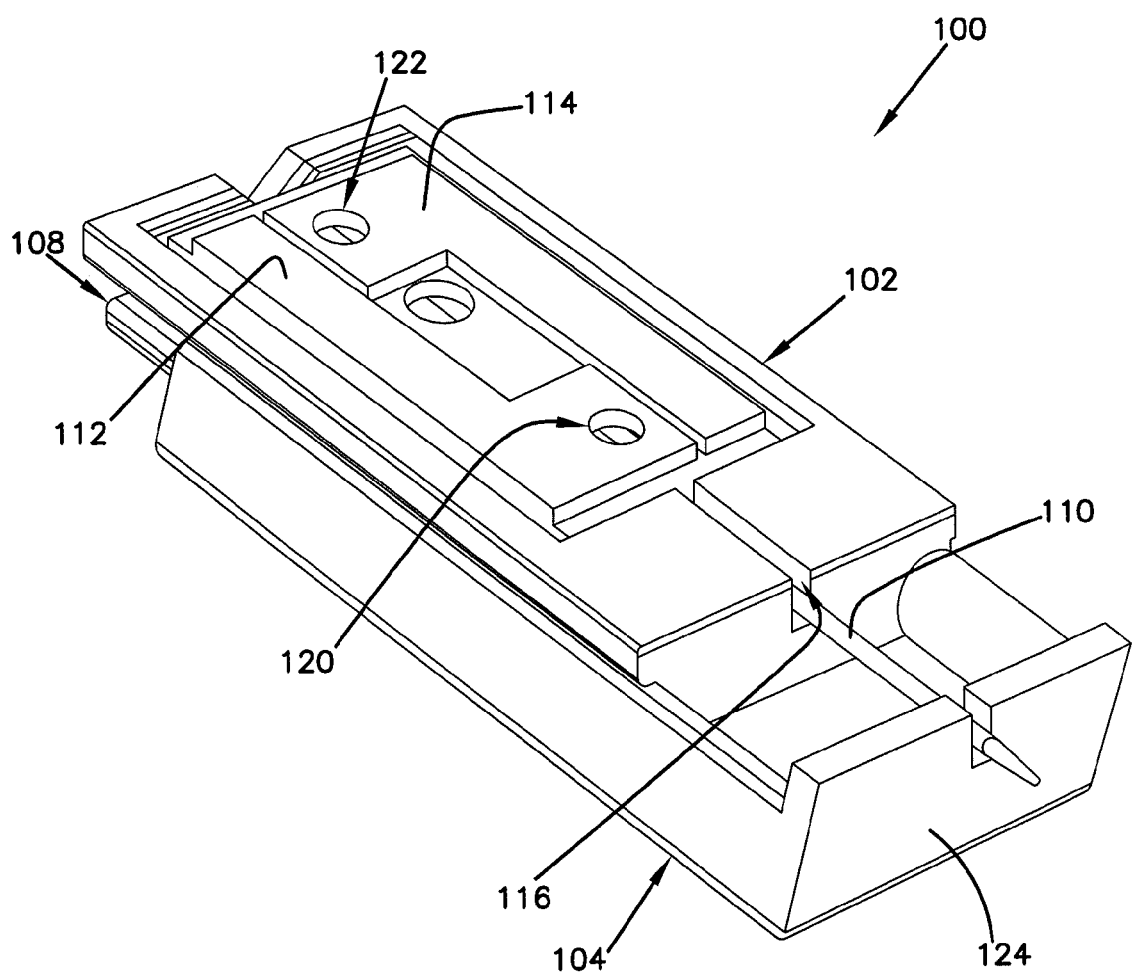
FIG. 1 is perspective view of a sensor module in accordance with the principles of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The following definitions are provided for terms used herein:

A "working electrode" is an electrode at which the analyte (or a second compound whose level depends on the level of the analyte) is electrooxidized or electroreduced with or without the agency of an electron transfer agent.

A "reference electrode" is an electrode used in measuring the potential of the working electrode. The reference electrode should have a generally constant electrochemical potential as long as no current flows through it. As used herein, the term "reference electrode" includes pseudo-reference electrodes. In the context of the disclosure, the term "reference electrode" can include reference electrodes which also function as counter electrodes (i.e., a counter/reference electrode).

A "counter electrode" refers to an electrode paired with a working electrode to form an electrochemical cell. In use, electrical current passes through the working and counter electrodes. The electrical current passing through the counter electrode is equal in magnitude and opposite in sign to the current passing through the working electrode. In the context of the disclosure, the term "counter electrode" can include counter electrodes which also function as reference electrodes (i.e., a counter/reference electrode).

A "counter/reference electrode" is an electrode that functions as both a counter electrode and a reference electrode.

An "electrochemical sensing system" is a system configured to detect the presence and/or measure the level of an analyte in a sample via electrochemical oxidation and reduction reactions on the sensor. These reactions are converted (e.g., transduced) to an electrical signal that can be correlated to an amount, concentration, or level of an analyte in the sample. Further details about electrochemical sensing systems, working electrodes, counter electrodes and reference electrodes can be found at U.S. Pat. No. 6,560,471, the disclosure of which is hereby incorporated herein by reference in its entirety.

"Electrolysis" is the electrooxidation or electroreduction of a compound either directly at an electrode or via one or more electron transfer agents.

An "electron transfer agent" is a compound that carries electrons between the analyte and the working electrode either directly or in cooperation with other electron transfer agents. One example of an electron transfer agent is a redox mediator.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both.

Figure 2:
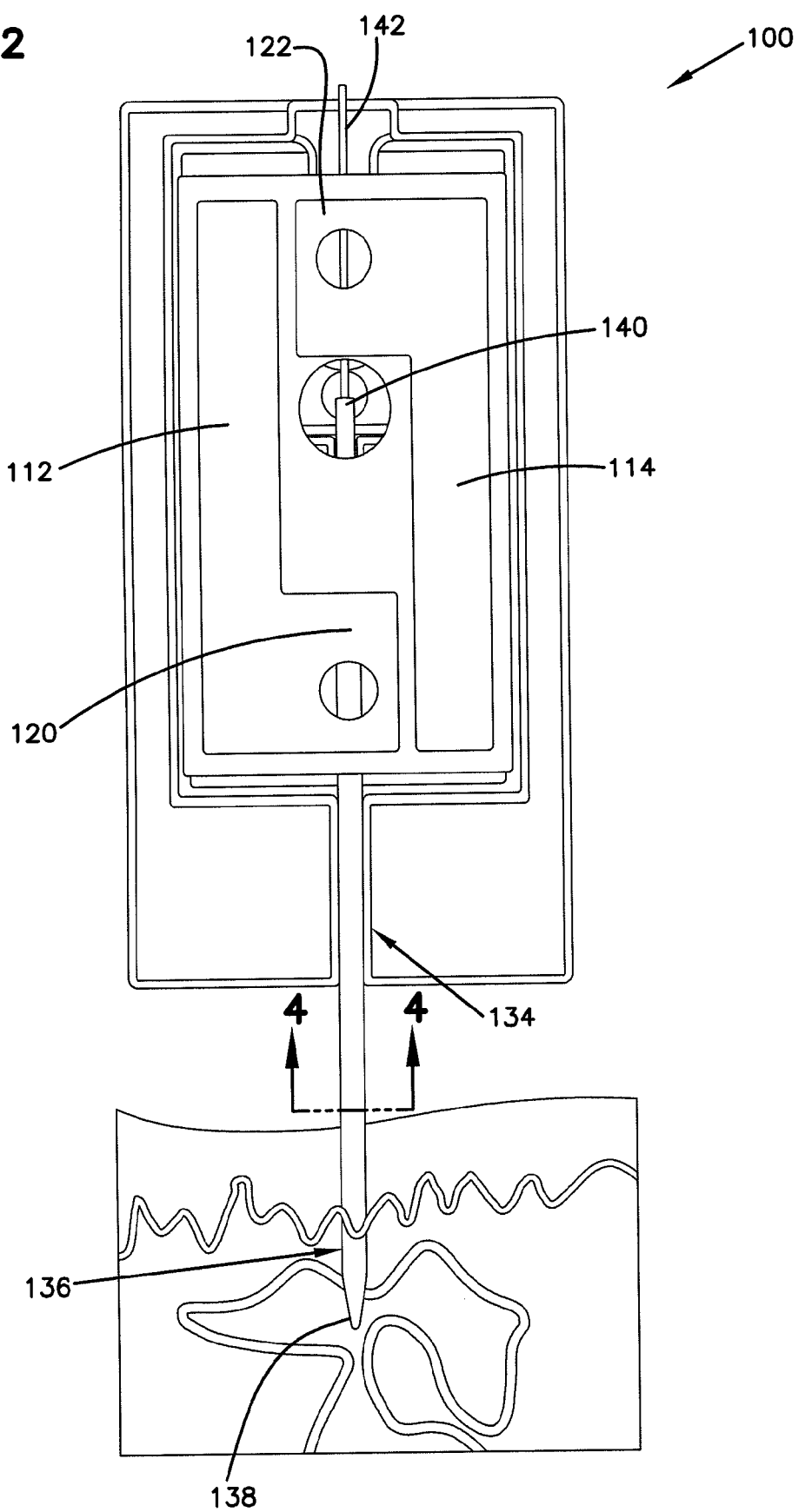
FIG. 2 is a top view of the sensor module of FIG. 1 with a skin piercing member of the sensor module in an extended position inserted in a vascular plexus.
Figure 3:
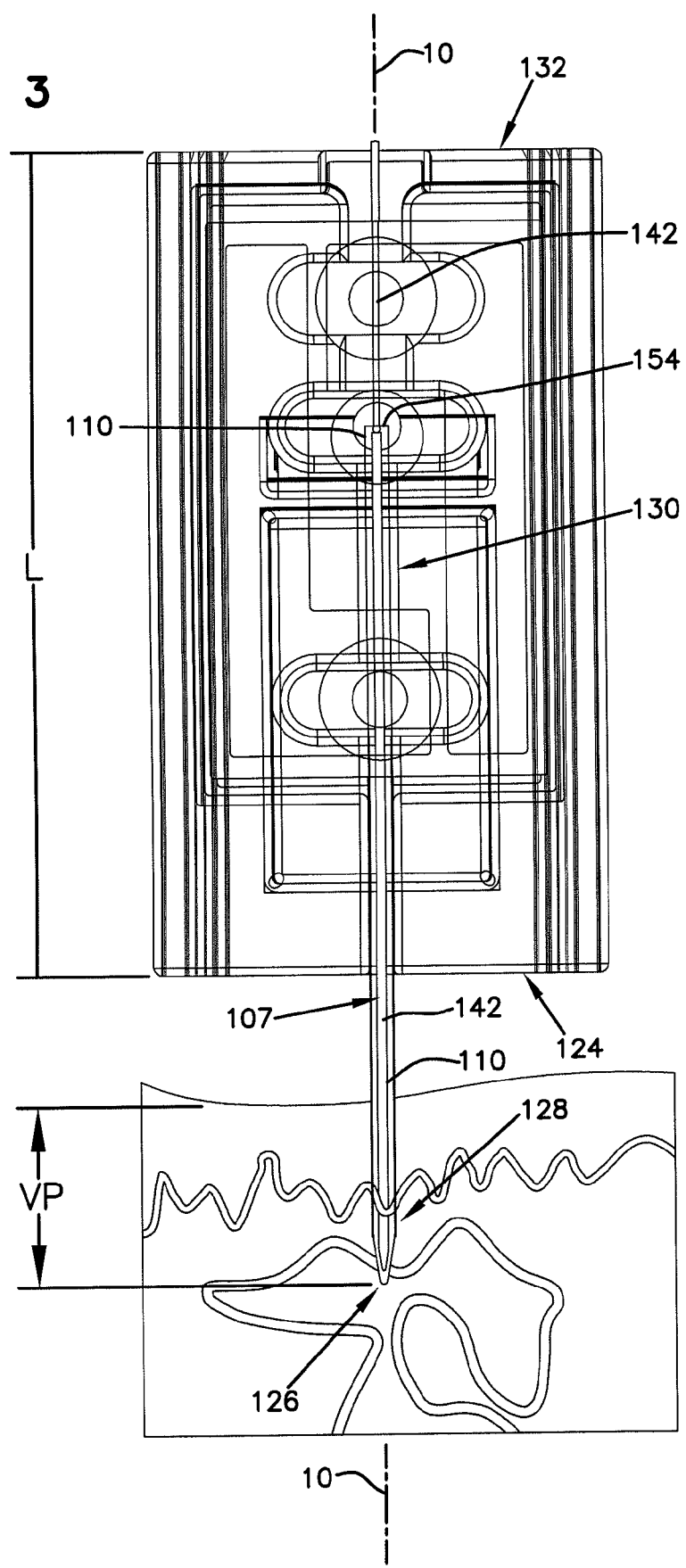
FIG. 3. is a plan view of the sensor module of FIG. 2 with various cross-section lines depicted.

FIGS. 1-3 are perspective views of an example of a sensor module 100. In this example, the sensor module 100 includes a carrier 102, a skin piercing member 110, a base 104 and two electrical contacts 112, 114. In FIG. 1, the skin piercing member 110 is shown in a retracted position.

The carrier member 102 is arranged and configured to slideably move along the base 104 within opposite channels 108 defined by the base 104. The channels 108 of the base 104 limit upward or downward movement of the carrier 102 relative to the base 104. The carrier 102 defines a first cavity 116 to mount the skin piercing member 110. In one example, the piercing member 40 is fixed relative to the carrier 102 such that the piercing member 40 is carried by the carrier 102 as the carrier 102 slides relative to the base 104. The carrier 102 is illustrated and described in more detail with reference to FIGS. 2-3.

The skin piercing member 110 extends along a length L of the carrier 102. The skin piercing member 110 is movable with the carrier 102 between a retracted position and an extended position (see FIG. 2) relative to the base. The skin piercing member 110 is illustrated and described in more detail with reference to FIGS. 2-4.

The electrical contacts 112, 114 mount on the carrier 102. The contacts 112, 114 respectively have contact tabs 120, 122. Tab 120 can be used to electrically connect the contact 112 to a reference electrode provided on an exterior surface of the member 110. Tab 122 can be used to electrically connect the contact 114 to a working electrode having a portion that extends into the piercing member 110 and a portion that extends axially outwardly from a base end of the piercing member 110. The contacts 112, 114 can include structures for electrically connecting the sensor module 100 to a sensor control system. In one example, the sensor control system applies a voltage across the working and reference electrodes and through a blood sample contained within a lumen of the skin piercing member 110. The reference electrode can be formed as a conductive layer provided on the outer surface of the skin piercing member 110. The electrical contacts 112, 114 are illustrated and described in more detail with reference to FIGS. 2-3.

FIGS. 2-3 illustrate features of the carrier 102.

In one example, the skin piercing member 110 is hollow and defines an interior lumen in which a working electrode is positioned. The working electrode can be formed by a conductive fiber or wire. A sensing layer can cover the conductive fiber or wire. A portion of the conductive fiber or wire covered with the sensing layer can form a sensing region located within a sample analysis zone contained entirely within the skin piercing member. The sample analysis zone 130 can provide for specific control of interrelated parameters such as active electrode area, response time, sensitivity, and drift to be engineered in as byproducts of static component features.

Figure 13:
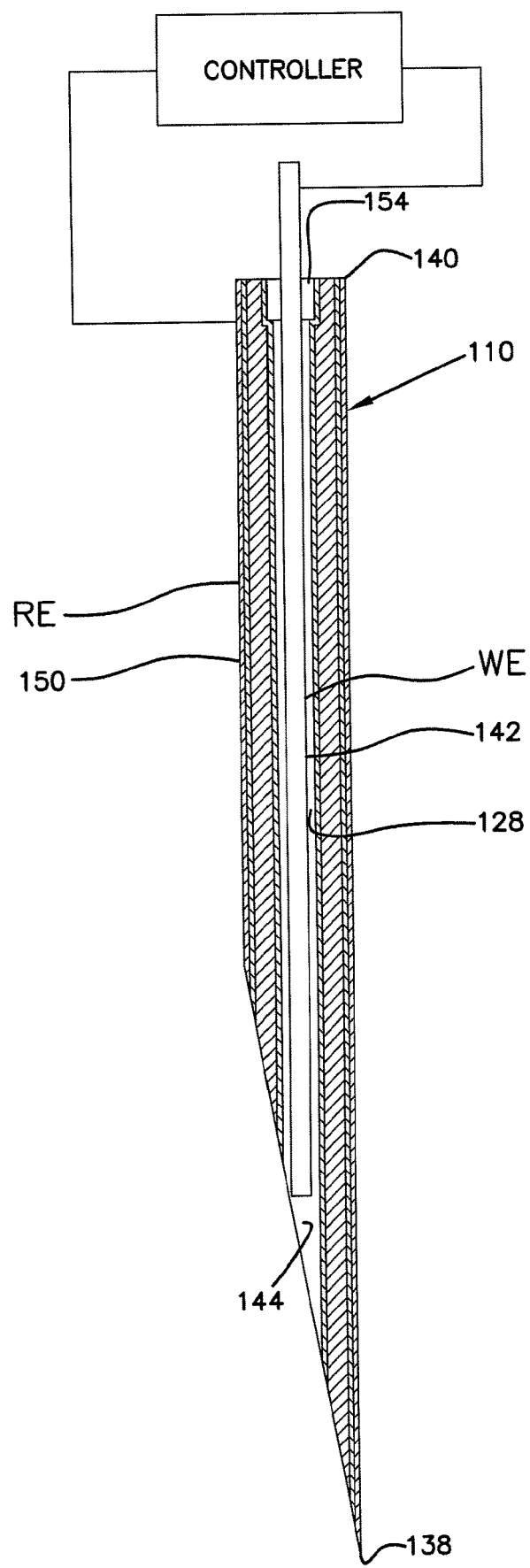
FIG. 13 is a schematic view of a skin piercing member, reference electrode and working electrode configuration of the sensor module of FIGS. 1-3.

FIG. 13 is a schematic view showing the skin piercing member 110 having the base end 140 and a tip end 138 (e.g., an insertion end). The skin piercing member 110 defines a lumen 144 that extends through the entire length of the skin piercing member 110 along an axis 10 (e.g., a skin piercing member axis or a lumen axis). A capillary stop can be provide adjacent the base end 140. The elongated working electrode 142 can include a conductive fiber or wire coated or otherwise covered with a sensing layer. The working electrode 142 is positioned within the lumen 144 and can have a lower end within 0.5 millimeters of the tip 138 and an upper end portion that extends out of the lumen 144. The conductive fiber or wire of the working electrode can be covered with a sensing layer suitable for sensing an analyte such as glucose. The skin piercing member 110 can include a conductive core material encapsulated within a dielectric layer that prevents electrical connections between the working electrode and the skin piercing member. A reference electrode can be supported on the dielectric outer surface of the skin piercing member. A control unit can be electrically connected to the reference and working electrodes.

In use, the skin piercing member is inserted into the skin to a depth less than 3 millimeters such that the tip 138 resides in the capillary bed. As so positioned, a first portion of the working electrode is subcutaneous and a second portion extends outside the body beyond the skin. Upon insertion, the combination of vascular pressure and capillary action causes blood to rapidly fill the lumen 144 and surround the portion of the working electrode within the skin piercing member 110. The blood flows up the lumen to the capillary stop. The volume of space defined within the skin piercing member from the tip to the capillary stop forms an analysis zone having a length that corresponds to a length of a wetted surface area of the sensing chemistry supported on the conductive fiber or wire of the working electrode. The capillary stop combined ensures that the wetted surface area is precisely controlled (i.e., the wetted length of sensor chemistry corresponds to the length of the working electrode that extends below the capillary stop). Applying a voltage between reference and working electrodes causes the oxidation/reduction of glucose in the analysis zone thereby generating a current at the working electrode which can be measured to sense a concentration of glucose in the blood sample. Control circuitry can apply the voltage, measure the current, and provide a display showing a reading indicating the glucose level.

The sensor module 100 is relatively compact and disposable. For example, the sensor module 100 is generally rectangular in shape and has a length that is less than 1 inch. The sensor module 100 includes opposite major sides and opposite minor sides that extend along the length of the sensor module 100.

The skin piercing member 110 of the sensor module 100 includes a skin piercing end 136 having a sharp tip 138 and a base end 140. The tip 138 of the skin piercing member 100 penetrates the skin of a patient and can be configured to provide a cutting action that generates a wound that self-closes upon removal of the piercing member 110 from the skin. The skin piercing member 110 can be a cannula, needle, or other similar structure preferably having a hollow interior. In this example, the sensor is configured to allow the analysis of the fluid sample to take place entirely within the skin piercing member 110. The skin piercing member 110 provides a volume or reservoir 107 for collecting blood received from a skin puncture site caused by the skin piercing member 110.

In one example, the skin piercing member 110 has a non-conductive construction. An example of a non-conductive construction includes a conductive base metal body (for strength) encased within a dielectric layer. The skin piercing member 110 includes a metal body 109 (FIG. 4) that can include a conductive metal, such as, but not limited to, stainless steel, and can be covered by a insulation layer 111 (FIG. 4), such as, but not limited to, parylene, acting to keep the conductive metal from creating a direct electrical pathway from a reference electrode to a working electrode of a two electrode sensor (e.g., a glucose sensor). The skin piercing member 110 can be about 30 gauge or less to allow for an insertion into a patient's skin tissue without creating either a blood producing wound or noticeable pain or discomfort upon insertion. The skin piercing member 110 can have a length of about 12 to 13 mm. In one example, only a relatively short length of the piercing member 100 extends beyond the base 102 when the carrier is slid to an extended position. In one example, the module 100 is configured such that the insertion depth of the skin piercing member 110 will not exceed 2 millimeters. In another example, the skin insertion depth of the skin piercing member 110 is in the range of about 1.5 to 2 mm. This depth of piercing allows for the sensor in the sensor module 100 to communicate with the vascular plexus (VP) dermal layer of tissue. At this depth, the sensor encounters capillary blood that is representative of cellular glucose.

In use of the sensor module 100, a contact end 124 of the base 104 is placed against a patient's skin at a sampling site where it is desired to take a fluid (e.g., blood) sample. Once the contact end 124 is in contact with the skin, the skin piercing member 110 is moved from the retracted position to the extended position (e.g., by sliding the carrier 102 relative to the base 104) thereby causing the tip 136 of the skin piercing member 110 to pierce the patient's skin. Upon insertion of the skin piercing member 110, blood from the capillary field fills the skin piercing member 110. Blood flow is caused at least in part by vascular pressure within the capillary bed. Capillary action also moves blood upwardly within the piercing member 110 to fill a sample analysis zone 130 within the piercing member 110. At the sample analysis zone 130, an analyte level (e.g., blood glucose level) in the blood sample is sensed through the use of a wired enzyme sensor arrangement including an elongated working electrode (WE) 142 (FIG. 4) positioned inside the piercing member 110. In certain embodiments, the electrode can be a fiber, wire, or other elongated member. In other embodiments, separate working, reference and counter electrodes can be provided in fluid communication with the sample analysis zone 130.

In some embodiments, a test is initiated by pressing an actuator button (not shown) on top of a meter (not shown) while holding the sensor module 100 on the test site (i.e., forearm or fingertip). This action causes a sequence of motions moving the sensor module 100 from a position within the sensor module 100 to an opening in the bottom of the meter. The meter can be placed on the approved testing site, (i.e., forearm or finger). The actuator button can be pressed again following a prompt causing the carrier 102 of the sensor module 100 carrying the skin piercing member 110 to move rapidly forward inserting the skin piercing member 110 to a prescribed depth. The skin piercing member 110 of the sensor module 100 enters a depth in tissue where a capillary blood field is encountered. The skin piercing member 110 stops at a capillary depth of about less than 3 mm below the skin surface and can reside for about less than 3 seconds to acquire a blood sample. The sample can be presented to the sensor module 100 by a rapid microfluidic flow initiated automatically by a combination of vascular blood pressure and capillary action. The sensor module 100 requires no other active mechanism to obtain a blood glucose value resulting in a passive system. Once the test is performed or completed, the carrier can be disposed by the user.

In one embodiment, the working electrode can include an elongated member that is coated or otherwise covered with a sensing layer and the reference/counter electrode can include any elongated member, such as a wire or fiber that is coated or otherwise covered with a layer, such as silver chloride. Preferably, at least a portion of each elongated member is electrically conductive. In certain embodiments, each elongated member can include a metal wire or a glassy carbon fiber. In still other embodiments, each elongated member can each have a composite structure and can include a fiber having a dielectric core surrounded by a conductive layer suitable for forming an electrode. The core can be made of medical grade polyetheretherketone.

An example composite fiber is sold under the name Resistat® by Shakespeare Conductive Fibers LLC. This composite fiber includes a composite nylon, monofilament, conductive thread material made conductive by the suffusion of about a 1 micron layer of carbonized nylon isomer onto a dielectric nylon core material. The Resistat® material is comprised of isomers of nylon to create the basic 2 layer composite thread. However, many other polymers are available for the construction, such as: polyethylene terephthalate, nylon 6, nylon 6,6, cellulose, polypropylene cellulose acetate, polyacrylonitrile and copolymers of polyacrylonitrile for a first component and polymers such as of polyethylene terephthalate, nylon 6, nylon 6,6, cellulose, polypropylene cellulose acetate, polyacrylonitrile and copolymers of polyacrylonitrile as constituents of a second component. Inherently conductive polymers (ICP) such as doped polyanaline or polypyrolle can be incorporated into the conductive layer along with the carbon to complete the formulation. In certain embodiments, the ICP can be used as the electrode surface alone or in conjunction with carbon. The Resistat® fiber is availability in diameters of 0.0025 to 0.016 inches, which is suitable for sensor electrodes configured in accordance with the principles of the present disclosure. Example patents disclosing composite fibers suitable for use in practicing sensor modules configured in accordance with the principles of the present disclosure include U.S. Pat. Nos. 3,823,035; 4,255,487; 4,545,835 and 4,704,311, which are hereby incorporated herein by reference in their entireties.

The sensing layers provided at working electrodes of sensor modules configured in accordance with the principles of the present disclosure can include a sensing chemistry, such as a redox compound or mediator. The term redox compound is used herein to mean a compound that can be oxidized or reduced. Example redox compounds include transition metal complexes with organic ligands. Preferred redox compounds/mediators include osmium transition metal complexes with one or more ligands having a nitrogen containing heterocycle such as 2,2'-bipyridine. The sensing material also can include a redox enzyme. A redox enzyme is an enzyme that catalyzes an oxidation or reduction of an analyte. For example, a glucose oxidase or glucose dehydrogenase can be used when the analyte is glucose. Also, a lactate oxidase or lactate dehydrogenase fills this role when the analyte is lactate. In sensor systems, such as the one being described, these enzymes catalyze the electrolysis of an analyte by transferring electrons between the analyte and the electrode via the redox compound. Further information regarding sensing chemistry can be found at U.S. Pat. Nos. 5,264,105; 5,356,786; 5,262,035; and 5,320,725, which were previously incorporated by reference in their entireties.

In one embodiment, the skin piercing member 110 defines a lumen 144 that extends along an elongated axis 10 from the skin piercing end 136 of the skin piercing member 110 toward the base end 140. The elongated working electrode 142 is positioned within the lumen 144. The elongated working electrode 142 has a length that extends along the lumen axis 20 and at least a section of the elongated working electrode 142 is positioned within the sample analysis zone 130. The elongated working electrode 142 includes the sensing chemistry.

The interaction of the skin piercing member 110 in concert with microfluidic forces (e.g., surface tension) within the lumen 144 promotes capillary flow of blood. Flow is initiated by ambient capillary pressure at the proximal lumen of the skin piercing member 110 when the piercing member is inserted into the papillary dermis to a depth of between 1-2 mm below the skin. Flow may also be promoted by the treatment of the lumen 144 with a surfactant compound. When so prepared, the combined factors create a driving mechanism to enable a spontaneous flow of capillary blood to enter the proximal lumen 144 and fill the skin piercing member 110 throughout its length.

The capillary stop 154 is formed at the skin piercing member 110 to inhibit the spontaneous blood flow from exiting the skin piercing member 110 at the distal end of the lumen 144. The self-limiting action of the flow into the interior passage of the skin piercing member 110 facilitates the lumen 144 to function as both an analysis cell—defined by the volume of the skin piercing member 110 and the length of the wetted working electrode WE portion residing within the skin piercing member 110—and as a counter electrode component of a multi electrode electrochemical cell.

The lumen 144 of the piercing member 110 may be sized appropriately to the configuration of the electrode bundle within it so as to optimize the microfluidic forces affecting the rate of transport thru the passage to the capillary stop 154. The lumen length must extend far enough above the tissue so as to provide sufficient surface area of the working electrode WE to produce a specified minimal output current. However, the lumen length may not be excessive or the time required to fill the lumen will drop rapidly with falling capillary pressure and fluid resistance slowing the transport rate.

The above described configuration of the electrode array within the piercing member 110 allows the major portion of the electrode surface to remain above the skin line presenting only the diameter of the piercing member 110 to the enervated tissue of the papillary dermis. This configuration allows the effective current produced by the electrode within the piercing member 110 to be two orders of magnitude larger than a traditional implanted sensor occupying the same footprint within tissue. In certain examples, the electrodes have an operational radius of less than 0.15 mm and a length of between 10 mm and 20 mm.

Figure 4:
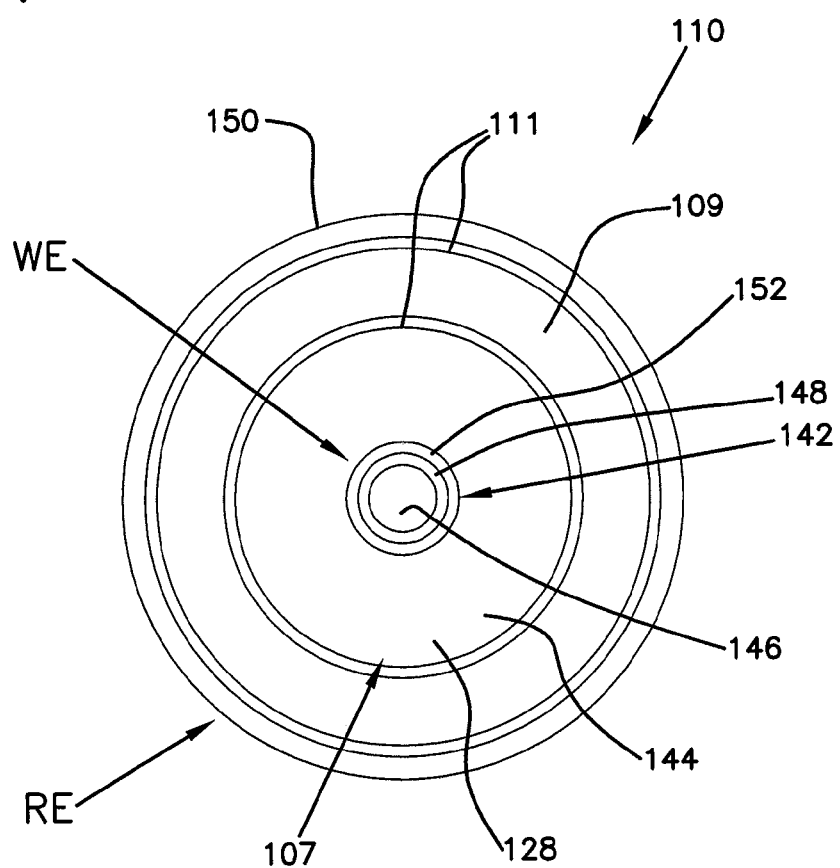
FIG. 4 is a cross-sectional view taken along line 4-4 of FIG. 2.

Referring to FIG. 4, a cross-sectional view of the skin piercing member 110 of the sensor module 100 is shown.

In this example, the elongated working electrode 142 is positioned within the lumen 144 of the skin piercing member 110 and includes a monofilament 146 (i.e., fiber) that can be coated with a conductive layer 148 (i.e., gold). The monofilament can be a polymeric material such as medical grade polyetheretherketone. The conductive monofilament 146 (fiber or wire) can have an outer diameter that is at least 10 percent as large as an outer diameter of the skin piercing member 110. The conductive layer 148 may be applied as a continuous Plasma Vacuum Deposition (PVD) process. The conductive layer 148 can be less than about 10 microns. The diameters of the multi-fiber composite can be between 0.001 inches and 0.004 inches. In this example, the elongated working electrode 142 may be coated in a secondary process step over the conductive layer 148 with glucose oxidase or other suitable enzyme chemistry. The elongated working electrode 142 may be inserted into the lumen 144 of the skin piercing member 110.

In this example, the skin piercing member 110 can include a conductive reference electrode (RE) layer 150 formed as a thick film of silver/silver chloride (Ag/Ag/Cl) on the insulated outer surface of the skin piercing member 110. The monofilament 146 (i.e., fiber) can be an aluminum conductive composite monofilament (CCM) with an enzyme sensing layer 152 which can serve as the elongated working electrode 142. The sensor module 100 can become active when an ionic fluid such as blood simultaneously contacts both the outer surface of the conductive reference electrode layer 150 (RE) and the elongated working electrode 142 (WE) completing an electrical circuit through the fluid path. Once the circuit is established by a passive process of rapid capillary flow into the lumen 144 of the skin piercing member 110, blood continues up a defined open passage space (less than 0.004 inches circumferential clearance) surrounding the fiber until encountering a capillary stop 154 feature formed at the base end 140 of the piercing member 110. The lumen 144 can be kept partially open at the base end 140 to serve as an air vent to promote the capillary flow.

In this example, the insertion end of the lumen 144 should be free of tissue plugs and reside at or below the vascular plexus (VP) between about 1 to 2 mm deep in the dermal layer where capillary vascular pressure is sufficient (about 14 to 22 mm Hg) to promote initial blood flow into the flow passage 128 of the skin piercing member 110. Capillary flow can augment external vascular pressure to rapidly sweep up the interior of the flow passage 128 to the capillary stop 154. Rapid autonomous and complete filling of the sample analysis zone 130—can be defined by the interior volume 107 of the skin piercing member 110 less the volume of the electrode within a space. This filling can be co-determinant of response time and is promoted by the addition of surfactants such as, but not limited to, Triton materials to either the skin piercing member 100 interior surface or to the detector chemistry or both.

In this example, the sample analysis zone 130 includes a controlled surface area of sensing chemistry that is wetted with blood during testing such that the entire controlled surface area is wetted when the analyte reading is taken. The controlled surface area is at least 10 times as large as a transverse cross-sectional area of the skin piercing member. In other embodiments, the controlled surface area can be at least 20 or 30 times larger than a transverse cross-sectional area of the working electrode.

Automation suitability can create a sensor configuration that will improve both quality of testing and the reliability of the test procedure for the consumer. The analysis zone method described can rely upon interdependent effects of defined part geometry, spatial relationships of components and specific transitional properties of the enzyme detector chemistry as it is hydrated by the incoming blood matrix. These factors in concert with the dynamic interaction of blood flowing into the cell in response to vascular pressure and capillary action function as the analysis zone method for establishing a rapid and self-limiting amperometric assay cell formed along a defined section of a long fiber.

Flow up the lumen 144 of the skin piercing member 110 can be within the microfluidic domain of non-Newtonian laminar flow. This transport dynamic up the circumferential channel 128 defined within the lumen 144 between the working electrode 142 and the inner surface of the skin piercing member 110 can be optimized by promoting low surface energy properties for the WE to allow complete and rapid wetting of the enzyme sensing layer 152. This surface property in turn can act in concert with the laminar flow dynamics to sweep the entire cavity containing the WE, free of air pockets that could otherwise unpredictably affect the area of blood in contact with the electrode surface causing irreproducible sensor performance.

The capillary pressure, the viscosity of the blood media plus the surface energy interactions of the electrode coating and the skin piercing member 110 inner wall surface in concert with the distance separating the surfaces can all impact micro capillary flow characteristics.

The capillary stop 154 can be a mechanism that limits further fluid flow along the enzyme sensing layer 152 forming the WE and provides for venting of air displaced by the rapid filling of the capillary space by blood. In this example, one functional characteristic of the WE is that the dry enzyme detector chemistry can be an effective insulator and can transition in phases from insulator to semiconductor to conductor as it becomes hydrated. This property prevents errant signal contributions to any portion of the CCM fiber kept dry during the time of the glucose assay. By defining the hydrated area of the WE through the combined use of the capillary stop 154 feature with mechanical control of the length of CCM fiber extending down into the skin piercing member passage 134. This method of defining electrode surface area provides for both manufacturing and functional advantages.

Referring again to FIGS. 2-3, the electrical contacts 112, 114 can be made of an electrically conductive material, such as, but not limited to, metals (i.e. copper, silver, aluminum, gold, bronze, and magnesium). During sample analysis at the sample analysis zone, a voltage can be applied between the working and reference electrodes. When the potential is applied, an electrical current will flow through the fluid sample to the working electrode. The current is a result of the oxidation or reduction of an analyte, such as glucose, in the volume of fluid sample located within the sample analysis zone. This electrochemical reaction occurs via the electron transfer agent in the enzyme sensing layer 152 and an optional electron transfer catalyst/enzyme in the enzyme sensing layer 152. By measuring the current flow generated at a given potential (e.g., with a controller described herein), the concentration of a given analyte (e.g., glucose) in the fluid sample can be determined. Those skilled in the art will recognize that current measurements can be obtained by a variety of techniques including, among other things, coulometric, potentiometric, perometric, voltometric, and other electrochemical techniques.

In this example, within a few hundredths of a second the defined sample analysis zone 130 is filled and the hydrating WE initiates an exchange electrons with the Ag/AgCl RE pattern on the non-conductive surface of the skin piercing member 110. A rising current appears at the data acquisition input of the sensor module 100 causing the software to start a countdown before initiating a data acquisition sequence for a prescribed number of discrete points (currently 500) taken at intervals over a set time window. The data set can be grouped by taking a mean of the discrete points. An area under the curve analysis can be applied to predict the plateau current for the sensor module 100. The correlation equates to a calibrated number representing a known glucose concentration at that current. The software then stores the value and can display it to the user on the meter LCD. The entire sequence from initiating actuator button to displayed blood glucose value requires less than 5 seconds. The result of the above testing sequence can be considered to be one reading.

In certain examples, the modules 100 are single use and each can be used to provide one glucose reading.

In certain embodiments, the data can be acquired using wireless device or portable electronic device (PED) such as, but not limited to, cellular phones. The PED can be used to act as a control unit for the sensor module 100. The sensor module 100 can be configured to interface with the PED which can store and display the glucose concentration to the user. In other embodiments, a separate test unit may be utilized to interface with a wireless device or PED (i.e., cellular phone). A chipset or similar component can be used in a glucose module to link to a PED via a broadband connection. The glucose test module can be connected automatically to the PED to initiate an application that would perform and display all the data management tasks. The glucose test module can be configured to have wide area network (WAN) capability to link to therapeutic software resident on other servers, such as, but not limited to, Cloud, that would completely automate the diabetics provisioning and treatment as well as link to a patient's physician or caregiver in real time. The glucose test module can be about 2.5 inch wide, about 3 inches long and about ¼ inch high.

Figure 5:
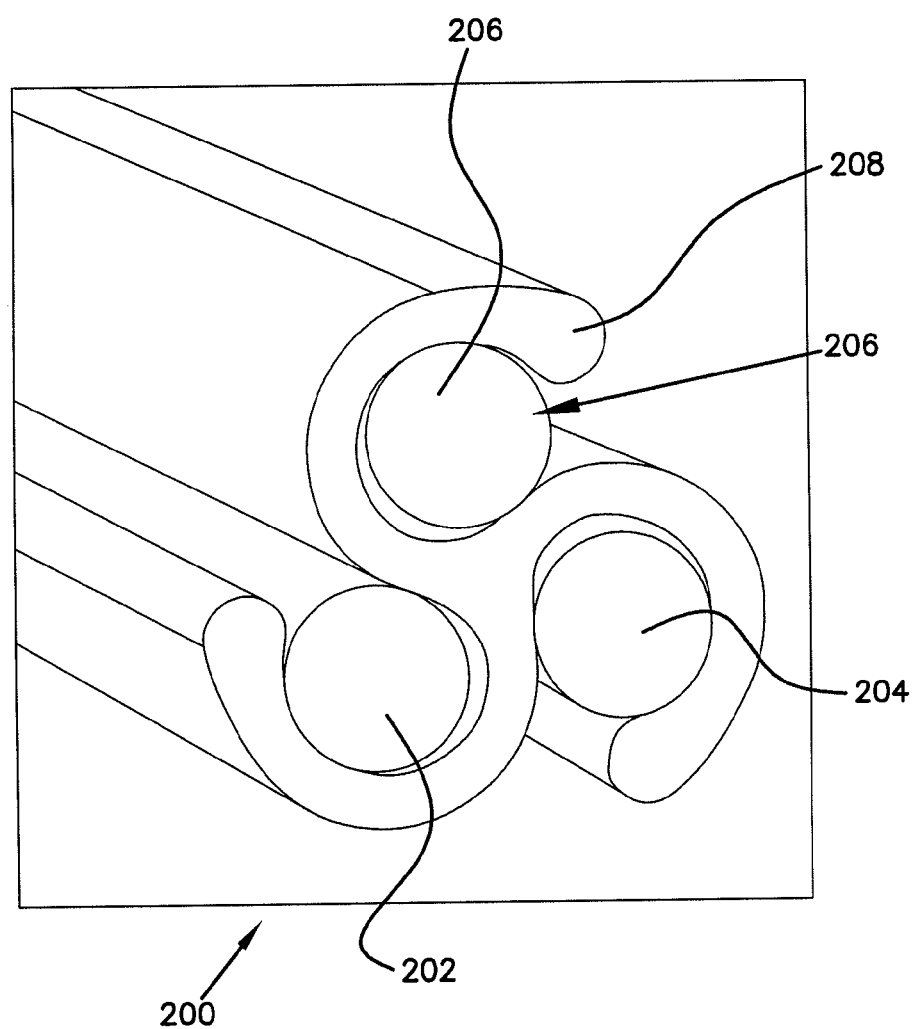
FIG. 5 is a perspective view of another embodiment of a sensor module with a three electrode profile in accordance with the principles of the present disclosure.

Referring to FIG. 5, a perspective view of another embodiment including three CCM electrodes 200.

In this example, the three CCM electrodes 200 are arranged and configured such that both RE and WE electrodes 202, 204 may be simultaneously inserted into a lumen of a skin piercing member. The skin piercing member is 29 gauge or smaller. The skin piercing member can have a size between approximately 28 gauge to 30 gauge, preferably a 30 gauge size in the example of home blood glucose testing.

Figure 6:
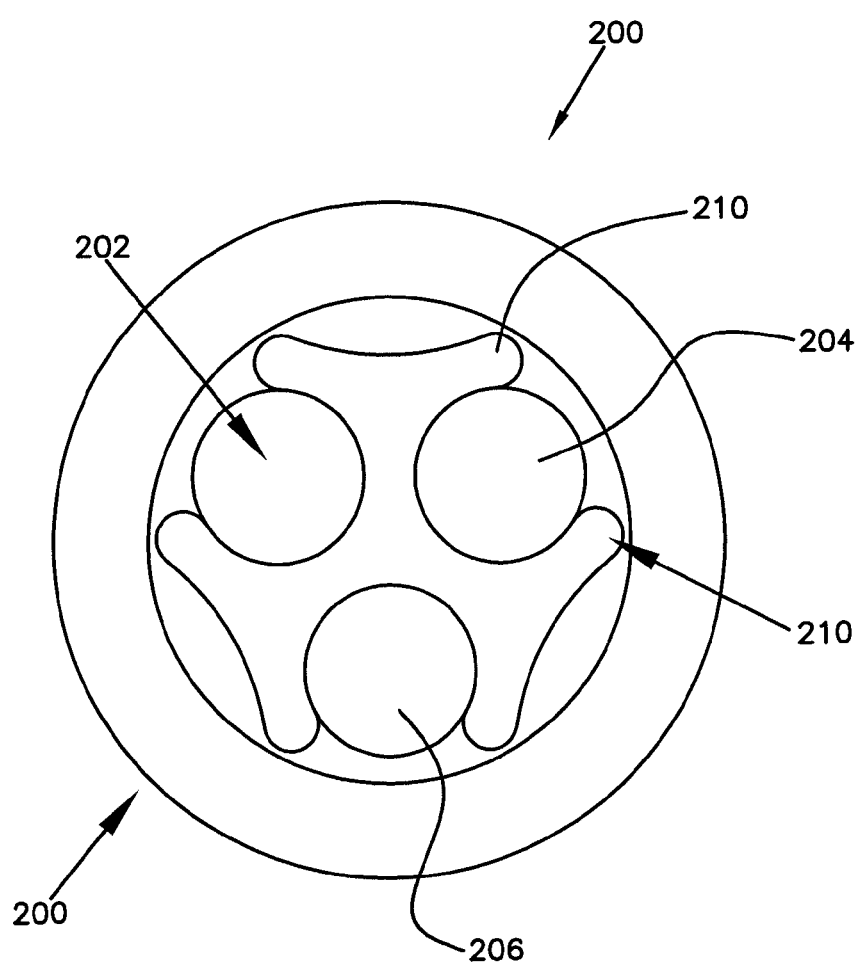
FIG. 6 is an alternate configuration of FIG. 5 with a different extrusion profile.

FIGS. 5-6 show the three CCM electrodes 200 or multi-electrode configurations that are assembled with two different profile extrusions, 208, 210 capable of insertion into a conductive needle, cannula or tube. In this example, the multi-electrode configuration does not need an insulated coating or a non-conductive piercing member as an RE electrode substrate; but may be only a piercing member, such as, but not limited to, a cannula, acting as the mechanical needle component. The piercing member can be made of a standard stainless steel material or similar material. The multi-electrode configuration may also be used as a catheter insert for continuous or remote monitoring applications.

The configuration of the multi-electrode may employ slightly different micro extrusion profiles as carriers for the three CCM electrodes 200, WE and RE fiber electrodes 202, 204. The micro extruded carrier profile is so designed in cross section as to maintain electrical isolation of the RE and WE 202,204—both from each other, and from the stainless steel piercing member (i.e., cannula). In some embodiments, the multi-electrode may have two working electrodes and one RE. The specific properties and profile extrusions 208, 210 (FIG. 6) combined with dedicated features incorporated into the extruded profile helps provide for unrestricted capillary flow up a flow passage of the skin piercing member, electrical isolation of the conductive components without the co-extrusion of the three CCM electrodes 200 that may be incompatible with such extrusion process, and combining four extrusion components into a single reel structure capable of insertion into the lumen of the skin piercing member. In this example, the profile may be configured to allow three or more electrodes to reside within a skin piercing member and operate as a three electrode enzymatic detection system.

The multi-electrode configuration allows for the ability to eliminate an Ag/Ag/Cl film coating for the RE 202 and substitute a composite Ag substrate fiber that can be fabricated in the same substrate materials and PVD process as the WE. The multi-electrode configuration can include a third electrode 206 (e.g., a supplemental electrode) that has no need for enzyme or detector chemistry. The third electrode 206 may be employed as a comparison means to determine what portion of the raw sensor current comes from interferent compounds such as vitamin C rather than from glucose. The comparison means can be a result of oxidizing those compounds at the bare Au surface and subtracting the apparent signal from the total sensor output. This function eliminates a developmental step in the electrode design and can help to resolve a common background noise problem for sensor accuracy. In other embodiments, additional electrodes beyond the three electrode profile may be added to the structure for the purpose of multi-parameter assays. Multi-parameter sensors providing more than two analyte targets for use in continuous monitoring can be fabricated. The supplemental electrode can also be used to defect other analytes (e.g., lactate) or to defect oxygen concentration.

Turning to FIG. 6, a top view of the three CCM electrodes 200 is shown. The fabrication of the profile extrusion 210 can be made by means of micro extrusion technology combined with continuous PVD technology as can be used in the gold coating process for CCM electrodes. The profile extrusions 208, 210 can be used to insulate the three CCM electrodes 200 from one another as well as from the interior wall of a skin piercing member. In this example, the extrusion profiles 208, 210 can be about 0.001 inches thick. The profiles can be configured to maximize fluid transport fully along the interior passage of the skin piercing member.

Figure 7:
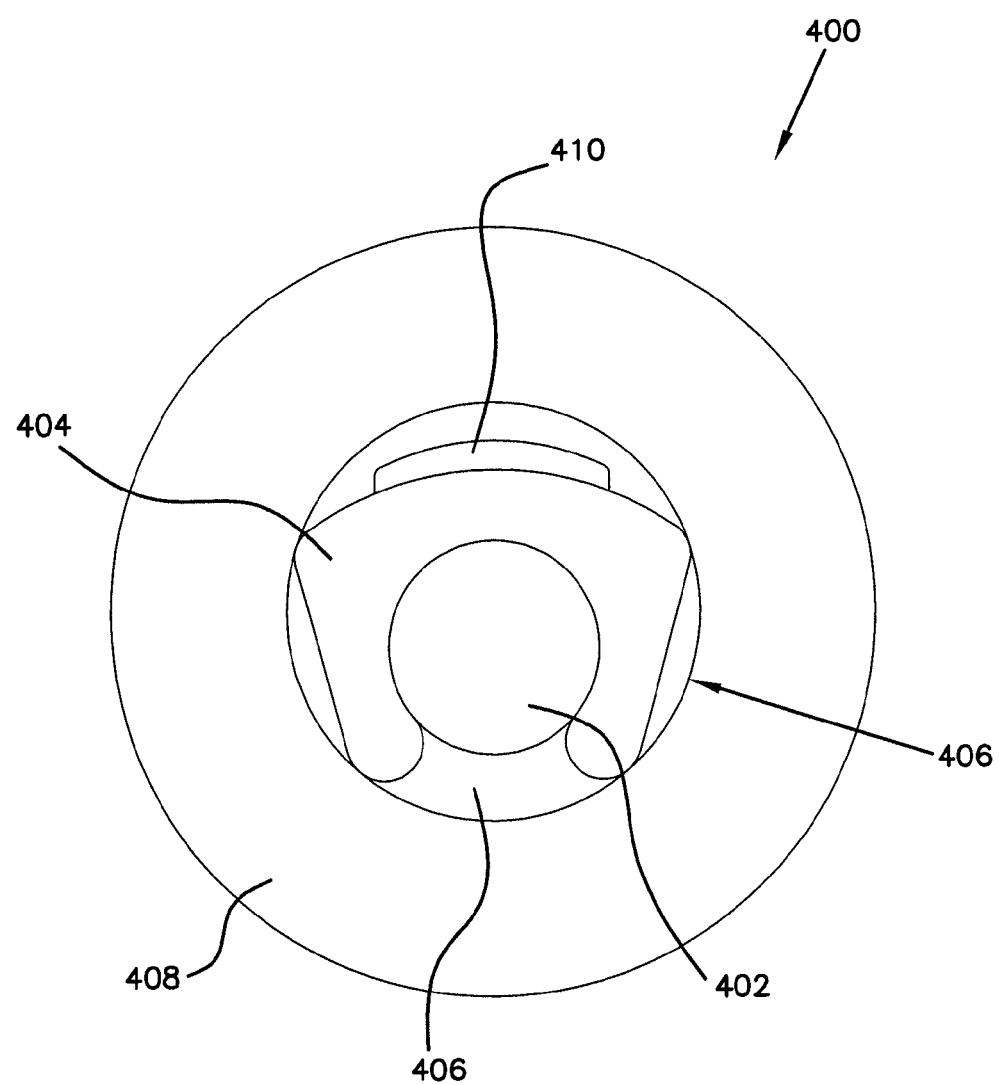
FIG. 7 is an end view of another embodiment of a sensor module with a two electrode profile.

Referring to FIG. 7, a perspective view of a two electrode 400 configuration for a sensor module is shown.

In this example, the two electrodes 400 configuration includes a monofilament 402 (i.e., fiber). The monofilament 402 can be insulated using an insulating substrate layer 404 similar to the embodiments described above. The monofilament 402 is capable of insertion into a lumen 406 of a skin piercing member 408. As shown, an AgAg/Cl layer 410 can be applied directly onto the insulating substrate layer 404.

Figure 8:
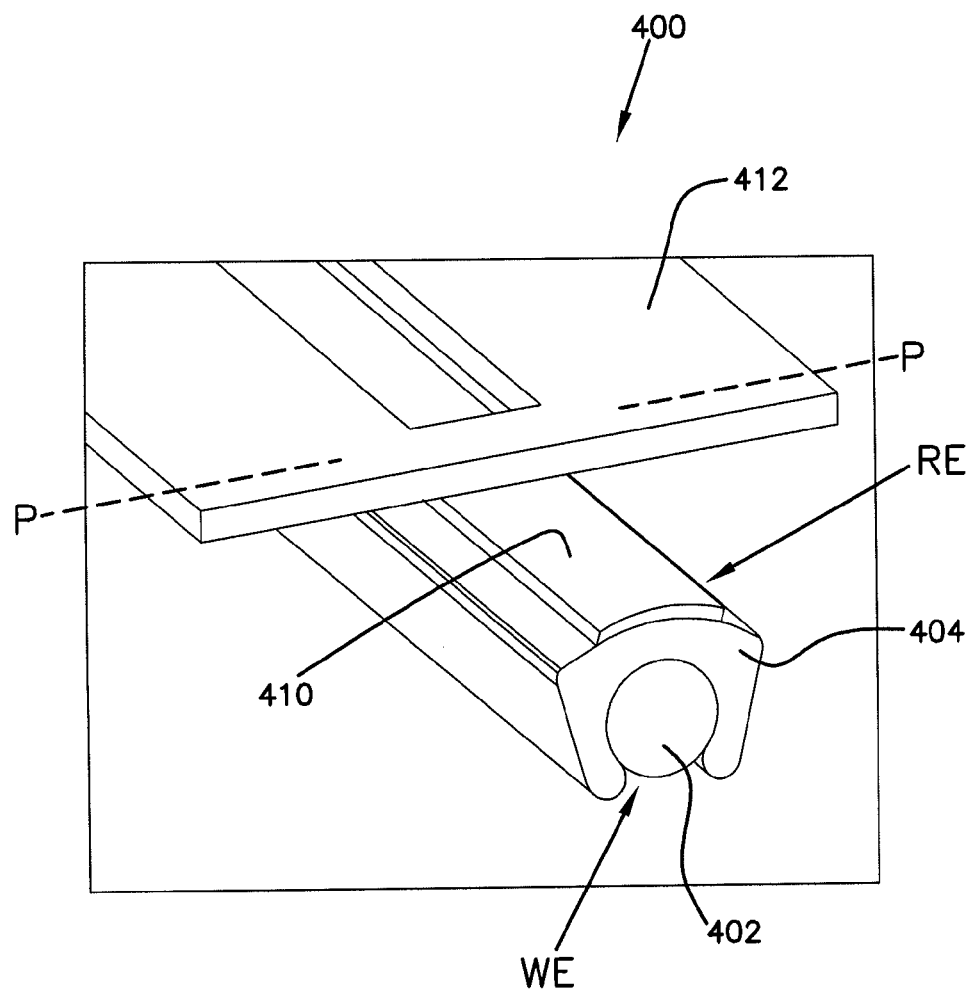
FIG. 8 is a perspective view of the two electrode profile of FIG. 7 with a mask.

Referring to FIG. 8, a perspective top view of the two electrodes 400 configuration is shown.

Figure 9:
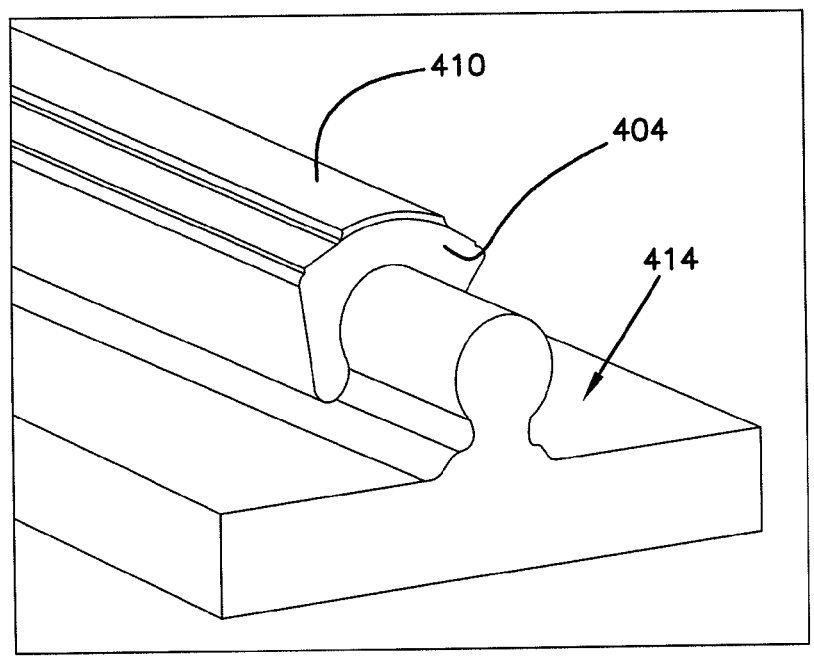
FIG. 9 is a perspective view of the two electrode profile of FIG. 7 with an electrode guide.
Figure 10:
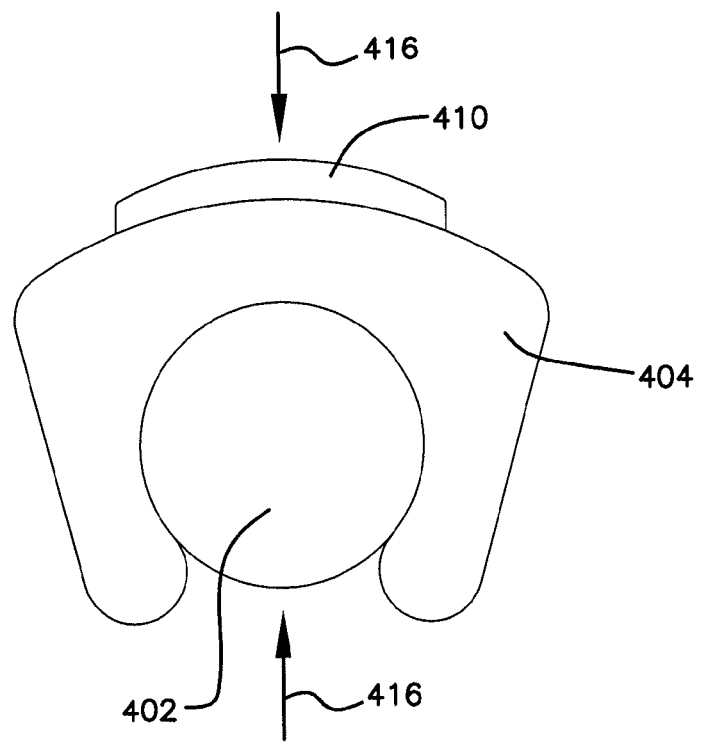
FIG. 10 is an end view of a portion of FIG. 7.
Figure 11:
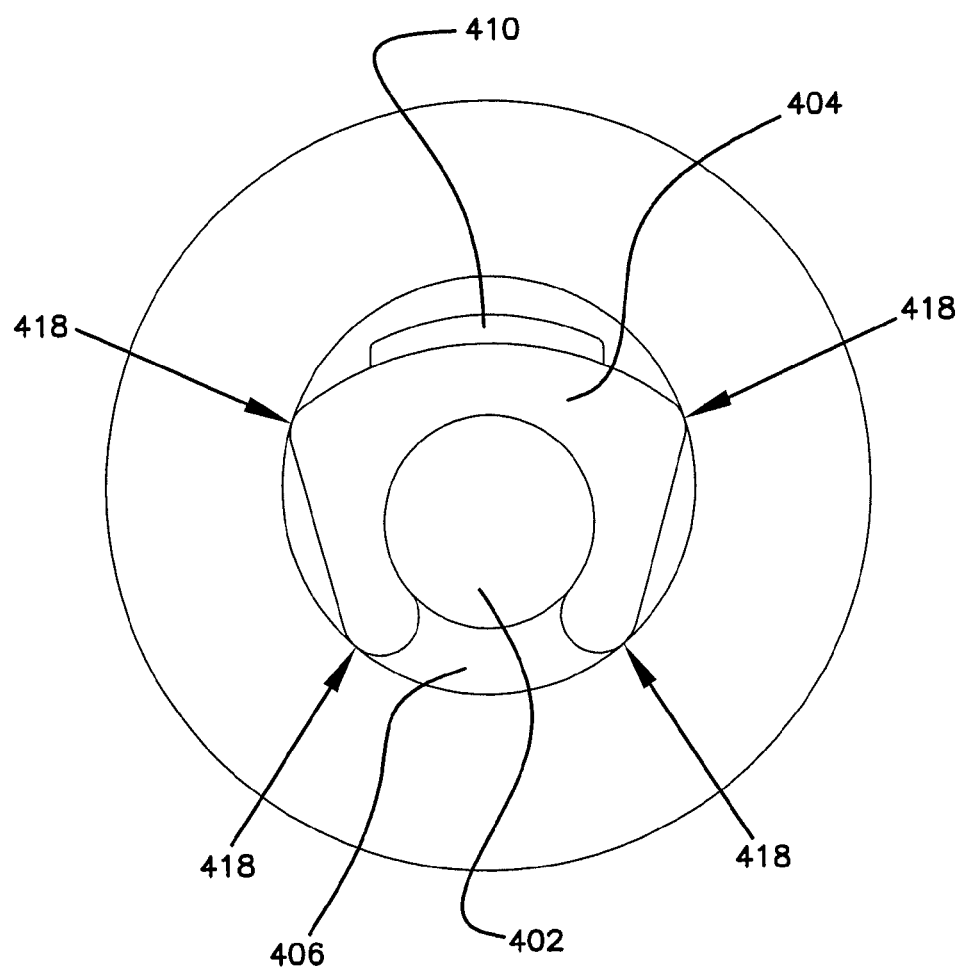
FIG. 11 is an end view of the two electrode profile of FIG. 7 with contact points depicted.

The AgAg/Cl layer 410 can be applied using fixtures and/or masks 412 to direct a plasma deposition of silver (Ag) travelling perpendicular to the plane P of the mask 412 onto a single surface of the profile for forming the RE. FIG. 9 shows an electrode guide 414 that can be used to help control the position of the profile in transit through the PVD process. The profile having the AgAg/Cl layer 410 deposition surface can act as the RE and the CCM monofilament 402 (i.e., fiber) coated with enzyme chemistry provides the WE function. FIG. 10 depicts arrows 416 that show features that can guide the profile and prevent both the RE and WE from contacting the conductive surface of the skin piercing member 408. FIG. 11 show contact points 418 that can be opposing where output contact features can impinge a sensor module and acquire a signal.

Figure 12:
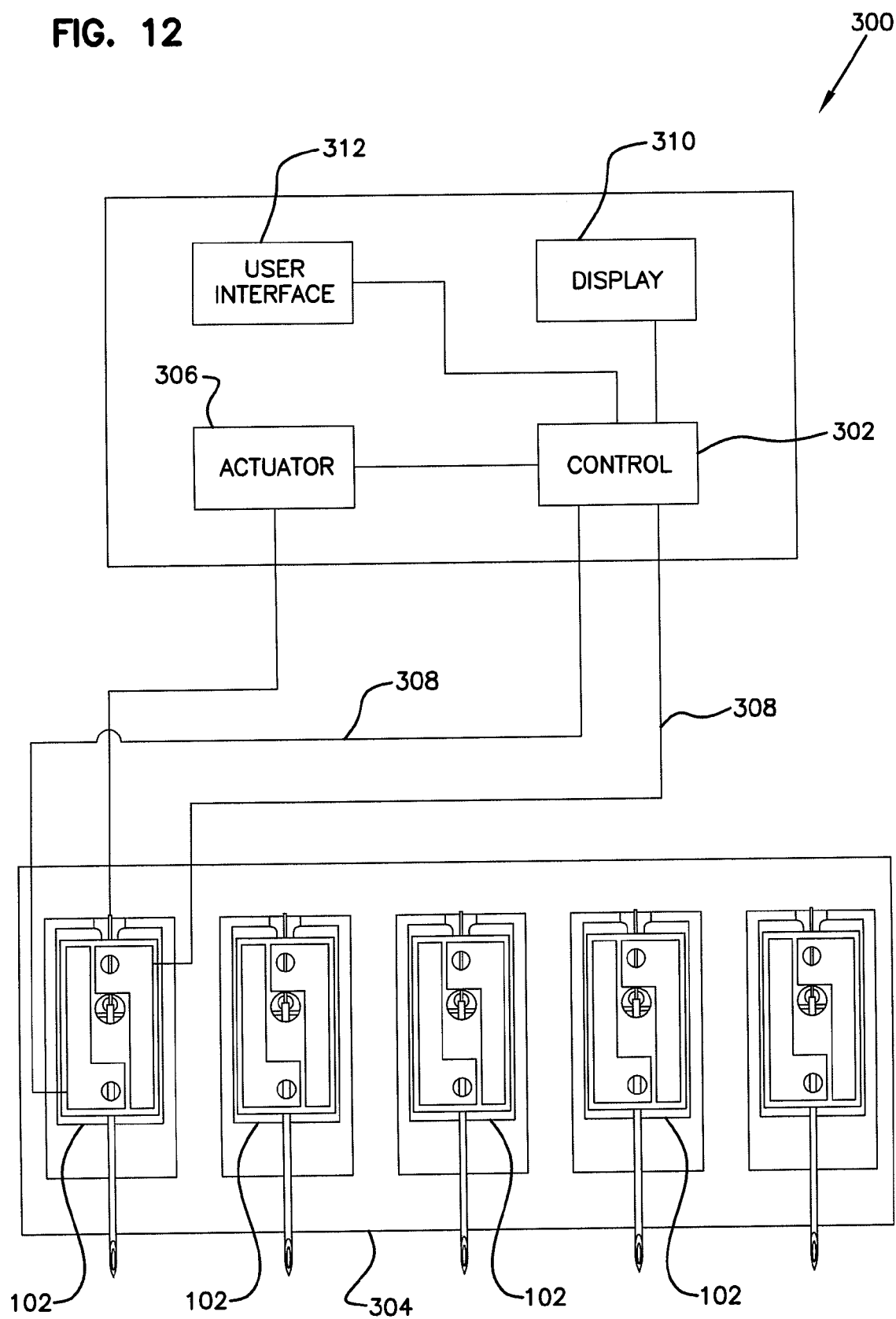
FIG. 12 is a schematic view of a sensing unit in accordance with the principles of the present disclosure that incorporates a plurality of the sensing modules of FIG. 1.

Referring to FIG. 12, a schematic of an analyte monitoring unit 300 is shown. The unit 300 where the modules 100 may be arrayed within a cartridge designed to provide a supply of multiple sensors that may be directly positioned on the skin of a patent's forearm or fingertip in order to obtain a blood glucose concentration. It will be appreciated that one or more sensor modules 100 can be incorporated as sub-components into an analyte monitoring unit 300. The unit 300 includes a controller 302 that couples to a module holder 304. The module holder 304 is configured to hold one or more sensor modules 100. Each sensor module 100 is configured to obtain one or more fluid samples, to measure a concentration level for one or more analytes (e.g., glucose, lactate, etc.), and to generate a signal (e.g., an electrical signal) indicating the concentration level. For example, the module holder 304 shown in FIG. 7 contains five sensor modules 100. In one embodiment, each sensor module 100 is configured to analyze a single fluid sample. In such an embodiment, the sensor module 100 can be removed from the module holder 304 after one use. In other embodiments, each sensor module 100 can be configured to analyze a greater number of fluid samples.

In general, the unit 300 includes a controller 302, an actuator 306, and input lines 308. The controller 302 controls the actuator 306 for driving the skin piercing members 110 of each sensor module 100 between the extended and retracted positions to obtain a fluid sample. The controller 302 can include a microcontroller, a mechanical controller, software driven controller, a hardware driven controller, a firmware driven controller, etc. The controller can include a microprocessor that interfaces with memory.

The controller 302 instructs the actuator 306 when to operate the sensor module 100 to obtain a fluid sample for analysis. The controller 302 also can instruct the module holder 304 and/or the actuator 306 to eject the used sensor module 100.

The input lines 308 carry the data/signals/readings (e.g., voltage values) generated at the elongated working electrode 142 of the sensor module 100 during analysis of a fluid sample to the controller 302 for analysis. The controller 302 converts the signals to an analyte concentration level (e.g., a blood glucose reading) or other desired information. The controller 302 causes the display 310 to indicate the processed information to the user. Other information also can be presented on the display 310. In one embodiment, the display 310 is a visual display. In other embodiments, an audio display also can be used. Additional information can be provided to the controller 302 via a user interface 312 (e.g., buttons, switches, etc.).

From the forgoing detailed description, it will be evident that modifications and variations can be made without departing from the spirit and scope of the disclosure.

What is claimed is:

1. A sensor module comprising:
a metal skin piercing member having a skin piercing end positioned opposite from a base end, the skin piercing member having an inner surface defining a lumen that extends along a length of the skin piercing member from the skin piercing end toward the base end, the lumen having a lumen axis, the metal skin piercing member being a needle;
a capillary flow stop for stopping capillary flow at a predetermined location within the lumen of the skin piercing member;
an electrode insert arrangement including an extruded, dielectric spacer and an elongated working electrode, the spacer including discrete portions configured to engage the inner surface of the skin piercing member to space the elongated working electrode from the inner surface of the metal skin piercing member to form a flow passage along the lumen of the skin piercing member, the electrode insert arrangement being positioned within the lumen so that the capillary flow passage extends between the working electrode and the inner surface of the skin piercing member, the extruded spacer having a non-circular cross-section taken across the lumen axis, the working electrode having a length that extends along the lumen axis, the working electrode including sensing chemistry that extends along the length of the working electrode between a tip of the skin piercing member and the capillary flow stop; and a blood sample analysis zone located entirely within the lumen of the skin piercing member, the blood sample analysis zone extending along a length corresponding to a length of a wetted surface area of the sensing chemistry of the working electrode.

2. The sensor module of claim 1, further comprising a base to which a carrier is mounted, wherein the carrier can slide relative to the base between a first position where the skin piercing end of the skin piercing member is exposed and a second position wherein the skin piercing member is retracted, wherein the skin piercing member extends no more than 3 millimeters beyond the base when in the first position, wherein the sensor module does not include an active means for drawing blood into the lumen, wherein the skin piercing member defines a diameter less than or equal to a 30 gauge needle.

3. The sensor module of claim 1, wherein the blood sample analysis zone extends for a majority of a length of the skin piercing member.

4. The sensor module of claim 1, further comprising a vent positioned at the capillary flow stop for venting of air displaced by rapid filling of a capillary space by blood.

5. The sensor module of claim 1 wherein the sensing chemistry is a dry sensing chemistry that is hydrated as the blood flows along the lumen, wherein the sensing chemistry is dielectric when dry, and transitions from semi-conductive to conductive as the sensing chemistry hydrates, and wherein the sensing chemistry includes glucose oxidase or glucose dehydrogenase.

6. The sensor module of claim 1, wherein the spacer includes an elongated micro extrusion that carries the working electrode and a reference electrode, wherein the micro extrusion maintains separation between the working electrode and the reference electrode and also separates the working and reference electrodes from the inner surface of the skin piercing member.

7. The sensor module of claim 6, wherein at least one of the electrodes is applied as a layer to the micro extrusion.

8. The sensor module of claim 1, wherein the sensor module is configured for a one time use in which one analyte reading is taken.

9. The sensor module of claim 1, wherein the sensor module is configured such that a first portion of the blood sample analysis zone is subcutaneous during testing and a second portion of the blood sample analysis zone is outside the body during testing.

10. The sensor module of claim 1, wherein the blood sample analysis zone has a controlled area of sensing chemistry that is at least 10 times as large as a transverse cross-sectional area of the skin piercing member.

11. The sensor module of claim 1, wherein the blood sample analysis zone has a controlled area of sensing chemistry that is at least 20 times as large as a transverse cross-sectional area of the skin piercing member.

12. The sensor module of claim 1, wherein the blood sample analysis zone has a controlled area of sensing chemistry that is at least 30 times as large as a transverse cross-sectional area of the skin piercing member.

13. The sensor module of claim 1, wherein the sensor module is configured such that a first portion of the working electrode is subcutaneous during testing and a second portion extends outside the body during testing, the first and second portions of the working electrode including the sensing chemistry.

14. The sensor module of claim 1, wherein the length of the blood sample analysis zone extends between the skin piercing end of the skin piercing member and the capillary flow stop.

15. The sensor module of claim 1, wherein the blood analysis zone within the skin piercing member fills passively.

16. The sensor module of claim 1, wherein the blood analysis zone within the skin piercing member fills passively when a tip of the skin piercing member is disposed in a capillary blood field less than 3 millimeters beneath skin of a user.

17. The sensor module of claim 1, wherein the elongated working electrode is formed by a conductive fiber or wire.

18. The sensor module of claim 1, wherein the length of the blood sample analysis zone extends for a majority of the elongated working electrode.

19. The sensor module of claim 1, wherein the elongated working electrode includes a first end portion that extends for a majority of a skin penetrating portion of the skin piercing member.

20. A sensor module comprising:
a skin piercing member having a skin piercing end positioned opposite from a base end, the skin piercing member having a length that extends from the skin piercing end to the base end of the skin piercing member, the skin piercing member defining a lumen that extends along the length of the skin piercing member, the skin piercing member being a metal needle;
a blood sample collection zone located entirely within the lumen of the skin piercing member, the blood sample collection zone including a volume for receiving blood that extends along the length of the skin piercing member for a majority of the length of the skin piercing member;
a vent for venting of air displaced by filling of the blood sample collection zone;
an elongate working electrode that extends longitudinally through the lumen, the elongate working electrode including a sensing portion including sensing chemistry, wherein the sensing portion of the elongate working electrode extends through the blood sample collection zone for a majority of the length of the skin piercing member;
an elongate extrusion disposed within the lumen of the skin piercing member, the elongate extrusion carrying the working electrode and also including discrete portions configured to separate the working electrode from an interior surface of the skin piercing member so that blood entering the lumen of the skin piercing member flows between the working electrode and the interior surface of the skin piercing member, the elongate extrusion extending outwardly past the based end of the skin piercing member and past the vent;
wherein the blood sample collection zone is configured to fill passively when the skin piercing end of the skin piercing member is disposed in a capillary blood field less than 3 millimeters beneath skin of a user; and
wherein the sensing portion of the working electrode is positioned within the blood sample collection zone such that a first section of the sensing portion of the working electrode is subcutaneous during testing and a second section of the sensing portion of the working electrode extends outside the body during testing.

21. The sensor module of claim 20, wherein the sensing chemistry is a dry sensing chemistry that is hydrated as the blood flows along the length of the skin piercing member though the blood sample collection zone, wherein the sensing chemistry is dielectric when dry, and transitions from semi-conductive to conductive as the sensing chemistry hydrates, and wherein the sensing chemistry includes glucose oxidase or glucose dehydrogenase.

22. The sensor module of claim 21, wherein the blood sample collection zone has a controlled area of sensing chemistry that is at least 10 times as large as a transverse cross-sectional area of the skin piercing member.

23. The sensor module of claim 21, wherein the blood sample collection zone has a controlled area of sensing chemistry that is at least 20 times as large as a transverse cross-sectional area of the skin piercing member.

24. The sensor module of claim 21, wherein the blood sample collection zone has a controlled area of sensing chemistry that is at least 30 times as large as a transverse cross-sectional area of the skin piercing member.

25. The sensor module of claim 20, wherein the skin piercing member defines an outer diameter less than or equal to a 30 gauge needle.

26. The sensor module of claim 20, wherein a reference electrode is carried by the elongate extrusion and extends along a majority of the length of the skin piercing member.

27. The sensor module of claim 20, wherein the sensing portion of the working electrode extends through an entire length of the blood sample collection zone.

28. A sensor module comprising:
a skin piercing member having a skin piercing end positioned opposite from a base end, the skin piercing member having an inner surface defining a lumen that extends along a length of the skin piercing member from the skin piercing end toward the base end, the lumen having a lumen axis;
a capillary stop disposed along the length of the skin piercing member, the capillary stop being configured to stop capillary flow along the length of the skin piercing member at a predetermined location within the lumen of the skin piercing member;
an electrode insert arrangement inserted within the lumen of the skin piercing member, the electrode insert arrangement including an elongate extruded spacer, a first electrode carried by the spacer, and a second electrode carried by the spacer, the spacer having a non-circular cross-section taken across the lumen axis, the first electrode being a working electrode disposed in a channel defined by the spacer, the second electrode including a conductive layer deposited on an externally-facing surface of the spacer, the first and second electrodes extending longitudinally along the spacer and being supported on the spacer in spaced relation relative to the inner surface of the lumen so that capillary flow entering into the skin piercing member flows between the first and second electrodes and the inner surface of the skin piercing member, the working electrode including sensing chemistry; and
a blood sample analysis zone located entirely within the lumen of the skin piercing member, wherein the working electrode extends longitudinally though the blood sample analysis zone from a location adjacent a tip of the skin piercing member to a location past the capillary stop, and wherein when the blood sample analysis zone is filled with blood, a wetted surface area of the sensing chemistry of the working electrode extends from the location adjacent the tip of the skin piercing member to the capillary stop.

29. A sensor module comprising:
a needle having a skin piercing end positioned opposite from a base end, the needle having an inner surface defining a lumen that extends along a length of the needle from the skin piercing end toward the base end, the lumen having a lumen axis;
a capillary stop disposed at the base end of the needle, the capillary stop being configured to stop capillary flow along the length of the needle at a predetermined location within the lumen of the needle;
an electrode insert arrangement inserted within the lumen of the needle, the electrode insert arrangement including:
an elongate spacer constructed of an extruded insulating material, the elongate spacer having a first portion disposed within the lumen of the needle and a second portion extending beyond the base end of the needle and beyond the capillary stop, the first portion defining an outwardly-facing electrode supporting surface that faces toward the inner surface of the needle; and
an elongate electrode deposited on the electrode supporting surface of the elongate spacer, the elongate electrode extending lengthwise along a length of the elongate spacer, the elongate electrode being supported on the elongate spacer in spaced relation relative to the inner surface of the needle so that a flow passage area is defined between the elongate electrode and the inner surface of the needle which is configured to allow capillary flow entering the needle through the skin piercing end to flow along the length of the needle through the flow passage area between the elongate electrode and the inner surface of the needle, the elongate spacer also including spacer portions that engage the inner surface of the needle at discrete locations to inhibit contact between the elongate electrode and the needle; and
a blood sample analysis zone located entirely within the lumen of the needle, wherein the elongate electrode extends longitudinally though the blood sample analysis zone from a location adjacent a tip of the needle to a location past the capillary stop.

30. The sensor module of claim 29, wherein elongate electrode is a first elongate electrode, wherein the electrode supporting surface is a first electrode supporting surface, wherein the flow passage area is a first flow passage area, wherein the elongate spacer includes a second electrode supporting surface that faces toward the inner surface of the lumen in a direction opposite from the first electrode supporting surface, wherein a second elongate electrode is supported on the second electrode supporting surface, and wherein the second elongate electrode is supported on the elongate spacer in spaced relation relative to the inner surface of the lumen so that a second flow passage area is defined between the elongate electrode and the inner surface of the lumen.

31. The sensor module of claim 30, wherein at least one of the first and second elongate electrodes is a working electrode including sensing chemistry, and wherein when the blood sample analysis zone is filled with blood, a wetted surface area of the sensing chemistry of the working electrode extends from the location adjacent the tip of the needle to the capillary stop.

* * * * *